(12) United States Patent
Guile

(10) Patent No.: US 7,384,951 B2
(45) Date of Patent: *Jun. 10, 2008

(54) THIENOPYRIMIDINEDIONES AND THEIR USE IN THE MODULATION OF AUTOIMMUNE DISEASE

(75) Inventor: Simon David Guile, Loughborough (GB)

(73) Assignee: AstraZeneca AB (SE)

( * ) Notice: Subject to any disclaimer, the term of this patent is extended or adjusted under 35 U.S.C. 154(b) by 0 days.

This patent is subject to a terminal disclaimer.

(21) Appl. No.: 10/542,197

(22) PCT Filed: Jan. 15, 2004

(86) PCT No.: PCT/SE2004/000052

§ 371 (c)(1),
(2), (4) Date: Jul. 14, 2005

(87) PCT Pub. No.: WO2004/065394

PCT Pub. Date: Aug. 5, 2004

(65) Prior Publication Data

US 2006/0052400 A1    Mar. 9, 2006

(30) Foreign Application Priority Data

Jan. 17, 2003 (SE) .................................. 0300119

(51) Int. Cl.
*A61K 31/519* (2006.01)
*C07D 496/04* (2006.01)
*A61P 11/06* (2006.01)

(52) U.S. Cl. ..................................... 514/260.1; 544/278
(58) Field of Classification Search ................. 544/278; 514/260.1
See application file for complete search history.

(56) References Cited

U.S. PATENT DOCUMENTS

| | | |
|---|---|---|
| 6,180,635 B1 | 1/2001 | Cheshire et al. |
| 6,232,320 B1 | 5/2001 | Stewart et al. |
| 6,300,334 B1 | 10/2001 | Bantick et al. |
| 6,342,502 B1 | 1/2002 | Cheshire et al. |
| 7,064,126 B2 | 6/2006 | Cooper et al. |
| 2004/0171623 A1 | 9/2004 | Reynolds et al. |
| 2004/0254198 A1 | 12/2004 | Reynolds et al. |
| 2006/0135539 A1 | 6/2006 | Guile et al. |

FOREIGN PATENT DOCUMENTS

| | | |
|---|---|---|
| WO | WO 98/54190 | 12/1998 |
| WO | WO 99/29695 | 6/1999 |
| WO | WO 00/12514 | 3/2000 |
| WO | WO 03/008422 | 1/2003 |
| WO | WO 03/011868 | 2/2003 |
| WO | WO 2004/065393 | 8/2004 |
| WO | WO 2004/065395 | 8/2004 |

OTHER PUBLICATIONS

"New Drugs for Asthma, Allergy and COPD," Prog. Respir. Res. Basel, Karger, 2001, vol. 31, pp. 212-216.*
Yamaguchi et al., "Novel Antiasthmatic Agents with Dual Activities of Thromboxane A$_2$ Synthetase Inhibition and Bronchodilation. V.[1])Thienopyridazinone Derivatives", *Chem. Pharm. Bull.* 43(2):236-240 (1995).
AllRefer.com Health entry for Chronic Obstructive Pulmonary Disease <<http://health.allrefer.com/health/chronic-obstructive-pulmonary-disease-prevention.html>> downloaded from the Internet Aug. 23, 2004.
BestHealth entry for ARDS (adult respiratory distress syndrome) <http://www.wfubmc.edu/besthealth/ency/article/000103prv.htm>.
Gupta et al., "Tacrolimus: a review of its use for the management of dermatoses", *J. Eur. Acad. Dermatol. Venereal.* 16:100-114 (2002).
MDAdvice.com entry for Asthma http://www.mdadvice.com/topics/asthma/info/1.htm downloaded from the internet Mar. 5, 2003.

(Continued)

*Primary Examiner*—Brenda L. Coleman
*Assistant Examiner*—Susanna Moore
(74) *Attorney, Agent, or Firm*—Fish & Richardson P.C.

(57) ABSTRACT

The invention relates to thienopyrimidinediones of formula (1) wherein $R^1$ and $R^2$ each independently represent a $C_{1-6}$alkyl, $C_{3-6}$alkyl, $C_{3-6}$alkenyl, $C_{3-5}$cycloalkyl$C_{1-3}$alkyl or $C_{3-6}$cycloalkyl; each of which may be optionally substituted by 1 to 3 halogen atoms $R^3$ is a group CO-G or $SO_2$-G where G is a 5- or 6-membered ring containing a nitrogen atom and a second heteroatom selected from oxygen and sulphur adjacent to the nitrogen; the ring being substituted by at least one group as defined in the specification, Q is $CR^4R^5$ where $R^4$ is hydrogen, fluorine or $C_{1-6}$ alkyl and $R^5$ is hydrogen, fluorine or hydroxy; and Ar is a 5-10-membered aromatic ring system wherein up to 4 ring atoms may be heteroatoms independently selected from nitrogen, oxygen and sulphur, the ring system being optionally substituted by one or more groups defined in the specification; as well as pharmaceutically acceptable salts and solvates thereof. Processes for their preparation of the compounds, pharmaceutical compositions containing them and their use in therapy, in particular in immunosuppressive therapy are also described

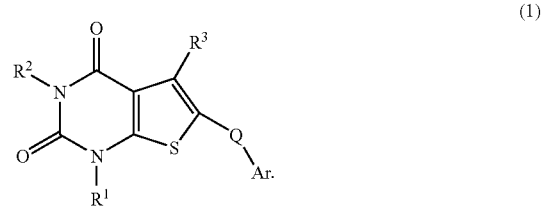

(1)

14 Claims, No Drawings

OTHER PUBLICATIONS

Meagher et al., "Atopic dermatitis: Review of immunopathogenesis and advances in immunosuppressive therapy", *Australas. J. Derm.* 43:247-254 (2002).

Perrett et al., "Cyclosporin in childhood psoriasis", *Journal of Dermatological Treatment* 14:113-118 (2003).

Tan et al., "Psoriasis", *Drugs of Today* 34(7):641-647 (1998).

Thestrup-Pedersen, "Tacrolimus treatment of atopic eczema/dermatitis syndrome", *Curr Opin Allergy Clin Immunol* 3:359-362 (2003).

Wolff et al., "Pimecrolimus for the treatment of inflammatory skin disease", *Expert Opin. Pharmacother.* 5:643-655 (2004).

Yamamoto et al., "Topical tacrolimus: an effective therapy for facial psoriasis", *Eur J Dermatol* 13:471-473 (2003).

Yu et al., "Refractory atopic dermatitis treated with low dose cyclosporin", *Annals of Allergy, Asthma & Immunology* 89:127-131.

BestHealth entry for ARDS (adult respiratory distress syndrome) <http://www.wfubmc.edu/besthealth/ency/article/000103prv.htm>, downloaded Mar. 5, 2003.

Yu et al., "Refractory atopic dermatitis treated with low dose cyclosporin", *Annals of Allergy, Asthma & Immunology* 89:127-131, (2002).

* cited by examiner

THIENOPYRIMIDINEDIONES AND THEIR USE IN THE MODULATION OF AUTOIMMUNE DISEASE

CROSS-REFERENCE TO RELATED APPLICATIONS

This application is the National Stage of International Application No. PCT/SE2004/000052, filed Jan. 15, 2004, which claims the benefit of Swedish Patent Application Serial No. 0300119-5, filed Jan. 17, 2003. The contents of both applications are hereby incorporated by reference in their entireties.

The present invention relates to thienopyrimidinediones, processes for their preparation, pharmaceutical compositions containing them and their use in therapy. The invention also relates to their use in the modulation of autoimmune disease.

T-cells play an important role in the immune response, however in auto-immune disease T-cells are inappropriately activated against particular tissues and proliferate, e.g. causing the inflammation associated with rheumatoid arthritis. Inhibition of the proliferation of T-cells is beneficial in the modulation of autoimmune disease. The present invention relates to compounds which are beneficial in the modulation of autoimmune disease.

In accordance with the present invention, there is provided a compound of formula (1):

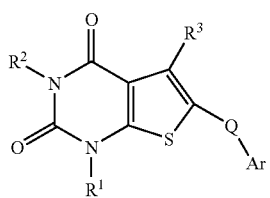

(1)

wherein:

$R^1$ and $R^2$ each independently represent a $C_{1-6}$alkyl, $C_{3-6}$alkenyl, $C_{3-5}$cycloalkyl$C_{1-3}$alkyl or $C_{3-6}$cycloalkyl; each of which may be optionally substituted by 1 to 3 halogen atoms;

$R^3$ is a group CO-G or $SO_2$-G where G is a 5- or 6-membered ring containing a nitrogen atom and a second heteroatom selected from oxygen and sulphur adjacent to the nitrogen; the ring being substituted by at least one group selected from halogen or $C_{1-4}$ alkyl, (which may be optionally substituted by up to five halogen atoms), and optionally substituted by up to a flirter 4 groups independently selected from halogen, hydroxyl and $C_{1-4}$ alkyl, (which may be optionally substituted by up to five halogen atoms);

Q is $CR^4R^5$ where $R^4$ is hydrogen, fluorine or $C_{1-6}$ alkyl and $R^5$ is hydrogen, fluorine or hydroxy;

Ar is a 5- to 10-membered aromatic ring system wherein up to 4 ring atoms may be heteroatoms independently selected from nitrogen, oxygen and sulphur, the ring system being optionally substituted by one or more substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, thioxo, nitro, cyano, —$N(R^6)R^7$ and —$(CH_2)pN(R^8)R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy, $SO_2N(R^6)R^7$, additionally Ar may be optionally substituted by a 5 or 6 membered aromatic ring containing up to 4 heteroatoms independently selected from nitrogen, oxygen and sulphur, and which is optionally substituted by one or more substituents independently selected from $C_{1-4}$alkyl (optionally substituted by 1,2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, thioxo, nitro, cyano, —$N(R^6)R^7$ and —$(CH_2)pN(R^8)R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy, $SO_2N(R^6)R^7$, p is 1, 2, 3 or 4;

$R^6$ and $R^7$ each independently represent a hydrogen atom, $C_{1-4}$alkanoyl or $C_{1-4}$alkyl, or together with the nitrogen atom to which they are attached form a 5- to 7-membered saturated heterocyclic ring; and $R^8$ and $R^9$ each independently represent a hydrogen atom, $C_{1-4}$alkanoyl or $C_{1-4}$alkyl, or together with the nitrogen atom to which they are attached form a 5- to 7-membered saturated heterocyclic ring;

and pharmaceutically acceptable salts and solvates thereof.

Alkyl groups, whether alone or as part of another group, can be straight chained or branched. They will generally comprise from 1 to 6 and suitably from 1 to 4 carbon atoms.

Examples of haloalkyl groups are halo$C_{1-4}$alkyl groups such as chloro- or fluoromethyl. Examples of dihaloalkyl groups are dihalo$C_{1-4}$alkyl groups such as difluoro- or dichloromethyl. Examples of trihaloalkyl groups are triha-lo$C_{1-4}$alkyl groups such as trifluoromethyl.

It will be understood that a compound of the formula (I) or a salt thereof may exhibit the phenomenon of tautomerism and that the drawings within this specification represent only one of the possible tautomeric forms. It is to be understood that the invention encompasses any tautomeric form.

It will be understood that a compound of the formula (1) or a salt thereof may exhibit the phenomenon of tautomerism and that the drawings within this specification represent only one of the possible tautomeric forms. It is to be understood that the invention encompasses any tautomeric form.

Preferably $R^1$ is $C_{1-6}$ alkyl or $C_{3-6}$ cycloalkyl. More preferably $R^1$ is ethyl, propyl, butyl or cyclopropyl. Most preferably $R^1$ is ethyl, isobutyl, isopropyl or cyclopropyl.

Preferably $R^2$ is $C_{1-6}$alkyl such as ethyl or methyl, more preferably methyl.

Suitably G in group $R^3$ is a 5-membered ring containing an oxygen atom, such as an isoxazolidinyl ring. Preferably the ring G is substituted by a $C_{1-4}$ alkyl group such as methyl. In a particular embodiment, the ring G is substituted by a $C_{1-4}$alkyl group such as methyl and by at least one additional substitutent selected from halogen, hydroxyl and $C_{1-4}$ alkyl, (which may be optionally substituted by up to five halogen atoms). In particular, the ring G is substituted by a $C_{1-4}$alkyl group and a hydroxy group, and preferably ring G is substituted by by methyl and a hydroxy substituent. A hydroxyl substituent may not be attached to a ring carbon atom that is bonded to a ring heteroatom.

The group G is preferably linked to the CO or $SO_2$ group through its ring nitrogen atom. Particular examples of the group G are is 4-hydroxy-4-methyl-isoxazolidin-2-yl.

Preferably $R^3$ is a group CO-G as defined above in which the ring G is linked via a nitrogen atom. More preferably $R^3$ is a group CO-G where G is a 5-membered ring as described above.

Most preferably $R^3$ is 4-hydroxy-4-methyl-isoxazolidin-2-yl carbonyl.

Suitably Q is $CR^5R^6$ where $R^5$ is hydrogen, $C_{1-6}$ alkyl and $R^6$ is hydrogen. Preferably Q is $CH_2$.

Examples of 5-10 membered mono- or bi-cyclic aromatic ring systems for Ar include thienyl, furanyl, pyrrolyl, pyrrolopyridino, imidazolyl, pyridyl, pyrazinyl, pyrimidyl, pyridazinyl, triazinyl, oxazolyl, thiazolyl, isoxazolyl, pyrazolyl, oxadiazolyl, thiadiazolyl, triazolyl, tetrazolyl and quinolyl. Particular examples are thienyl, pyrazolyl, thiazolyl or triazolyl ring, any of which may be optionally substituted.

A further example of Ar is phenyl, which may be optionally substituted as described above.

Where Ar is a bicyclic aromatic ring system, particular examples are a benzotriazole, pyrrolo[2,3-b]pyridine, quinoline ring or imidazopyridinyl ring, mid in particular a benzotriazole, pyrrolo[2,3-b]pyridine or a quinoline ring Suitably Ar is a 5-membered aromatic ring containing two heteroatoms optionally substituted as defined above or Ar is a 9- or 10-membered bicyclic ring containing one, two or three heteroatoms and optionally substituted as defined above. Preferably Ar is a 5-membered aromatic ring containing two heteroatoms optionally substituted as defined above.

Particular substituents for the group Ar are one or more substituents independently selected from $C_{1-4}$alkyl, halogen, haloalkyl, dihaloalkyl, trihaloalkyl, or a 5 or 6 membered aromatic ring containing up to 4 heteroatoms independently selected from nitrogen, oxygen and sulphur, which may itself be optionally substituted as described above, but in particular may be substituted by oxo.

For instance, Ar may be optionally substituted by one or more substituents selected from methyl, chloro, bromo, fluoro, trifluoromethyl, pyrimidinyl (such as 2-pyrimidinyl), pyridyl (such as 2-pyridyl or 4-pyridyl) or phenyl.

In a particular embodiment, Ar is a thienyl, pyrazole or thiazole ring each substituted by two or three alkyl, halogen, trifluoromethyl substituents and/or also substituted by a 2-pyrimidinyl or 2-pyridyl group.

A particular example of Ar is an optionally substituted pyrazole ring. Preferably Ar is a substituted pyrazole ring.

For instance, Ar is suitably a group of sub-formula (i)

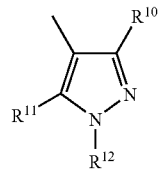

(i)

where $R^{10}$ and $R^{11}$ are independently selected from H, $C_{1-6}$alkyl, or halo$C_{1-6}$alkyl and $R^{12}$ is selected from H, $C_{1-6}$alkyl, or halo$C_{1-6}$alkyl or a 5- to 6-membered aromatic ring system wherein up to 3 ring atoms may be heteroatoms independently selected from oxygen, sulphur and nitrogen, which ring may be optionally substituted by one or more substituents independently selected from $C_{1-4}$alkyl (optionally substituted by 1,2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, oxo, thioxo, nitro, cyano, —N($R^6$)$R^7$ and —$(CH_2)$pN($R^8$)$R^9$, hydroxy, $C_{1-4}$alkylsulphonyl, $C_{1-4}$alkylsulphinyl, carbamoyl, $C_{1-4}$alkylcarbomyl, di-($C_{1-4}$alkyl)carbamoyl, carboxy, or $SO_2$ N($R^6$)$R^7$, where $R^6$, $R^7$, $R^8$, $R^9$ and p are as defined above.

In $R^{10}$ and $R^{11}$ are selected from H or $C_{1-3}$alkyl, such as methyl.

In particular, both $R^{10}$ and $R^{11}$ is $C_{1-3}$alkyl such as methyl.

Suitably $R^{12}$ is selected from H, $C_{1-3}$alkyl (such as methyl) or a 5- to 6-membered aromatic ring system wherein up to 3 ring atoms may be heteroatoms independently selected from oxygen, sulphur and nitrogen, optionally substituted by oxo. Where $R^{12}$ is a 5- to 6-membered aromatic ring system, particular examples of such systems are phenyl, pyridyl (such as 2-pyridyl or 4-pyridyl), pyrimidinyl (such as 2-pyrimidinyl) or thiazolyl (such as 2-thiazolyl).

Preferably $R^{12}$ is H, pyridyl or pyrimidinyl, and most preferably pyridyl or pyrimidinyl.

In an embodiment of the invention Ar is a pyrazole ring, substituted by alkyl such as $C_{1-6}$alkyl, or halo$C_{1-6}$alkyl such as or trifluoromethyl substituents and/or also substituted by a 2-pyrimidinyl or 2-pyridyl group.

Where $R^6$ and $R^7$ and $R^8$ and $R^9$ form a 5 to 7 membered saturated heterocyclic ring examples of suitable rings include morpholine, piperidine, piperazine and pyrrolidine.

Preferred compounds of formula (1) include:

(S)-2-[[6-[(3,5-Dimethyl-1H-pyrazol-4-yl)methyl]-1,2,3,4-tetrahydro-3-methyl-1-(2-methylpropyl)-2,4-dioxo-thieno[2,3-d]pyrimidin-5-yl]carbonyl]-4-methyl-4-isoxazolidinol, (S)-2-[[6-[(3,5-Dimethyl-1H-pyrazol-4-yl)methyl]-1,2,3,4-tetrahydro-3-methyl-1-(2-methylethyl)-2,4-dioxo-thieno[2,3-d]pyrimidin-5-yl]carbonyl]methyl-4-isoxazolidinol, 1-Cyclopropyl-6-[(3,5-dimethyl-1H-pyrazol-4-yl)methyl]-5-[[(4S-4-hydroxy-4-methyl-2-isoxazolidinyl]carbonyl]-3-methyl-thieno[2,3-d]pyrimidine-2,4(1H,3H)-dione, (S)-2-[[6-[(1H-1,2,3-Benzotriazol-1-yl)methyl]-1,2,3,4-tetrahydro-3-methyl-1-(1-methylethyl)-2,4-dioxo-thieno[2,3-d]pyrimidin-5-yl]carbonyl]-4-methyl-4-isoxazolidinol, (S)-2-[[6-[(4,5-Dichloro-2-methyl-1H-imidazol-1-yl)methyl]-1,2,3,4-tetrahydro-1-ethyl-3-methyl-2,4-dioxo-thieno[2,3-d]pyrimidin-5-yl]carbonyl]-4-methyl-4-isoxazolidinol, 5-[[(4S)-4-Hydroxy-4-methyl-2-isoxazolidinyl]carbonyl]-3-methyl-1-(2-methylpropyl)-6-(1H-pyrrolo[2,3-b]pyridin-3-ylmethyl)thieno[2,3-d]pyrimidine-2,4-(1H,3H)-dione, (4S)-4-methyl-2-[[1,2,3,4-tetrahydro-3-methyl-2,4-dioxo-1-propyl-6-(4-quinolinylmethyl)thieno[2,3-d]pyrimidin-5-yl]carbonyl]-4-isoxazolidinol, (4S)-2-[[6-[(2,4-Dichloro-5-thiazolyl)methyl]-1,2,3,4-tetrahydro-3-methyl-1-(2-methylpropyl)-2,4-dioxo-thieno[2,3-d]pyrimidin-5-yl]carbonyl]-4-methyl-4-isoxazolidinol, (4S)-2-[[6-[(3-Bromo-2-thienyl)methyl]-1,2,3,4-tetrahydro-3-methyl-1-(2-methylpropyl)-2,4-dioxo-thieno[2,3-d]pyrimidin-5-yl]carbonyl]-4-methyl-4-isoxazolidinol, 5-[[(4S)-4-Hydroxy-4-methyl-2-isoxazolidinyl]carbonyl]-3-methyl-1-(1-methylethyl)-6-[[5-methyl-3-(trifluoromethyl)-1H-pyrazolyl-4yl]-methyl]-thieno[2,3-d]pyrimidine-2,4(1H,3H)-dione, 6-[[3,5-Dimethyl-1-(2-pyridinyl)-1H-pyrazol-4-yl]methyl]-5-[[(4S)-4-hydroxy-4-methyl-2-isoxazolidinyl]carbonyl]-3-methyl-1-(1-methylethyl)thieno[2,3-d]pyrimidine-2,4(1H,3H)-dione, 5-[[(4S)-4-Hydroxy-4-methyl-isoxazolidinyl]carbonyl]-3-methyl-1-(1-methylethyl)-6-(1H-pyrrolo[2,3-b]pyridin-3-ylmethyl)-thieno[2,3-d]pyrimidine-2,4(1H,3H)-dione,
(4S-2-[[6-[[3,5-Dimethyl-1-(4pyridinyl)-1H-pyrazol-4-yl]methyl]-1,2,3,4-tetrahydro-3-methyl-1-(1-methylethyl)-2,4-dioxo-thieno[2,3-d]pyrimidin-5-yl]carbonyl]-4-methyl-4-isoxazolidinol,
(4S)-2-[[6-[[3,5-Dimethyl-1-(2-pyrimidinyl)-1H-pyrazol-4-yl]methyl]-1,2,3,4-tetrahydro-3-methyl-1-(1-methylethyl)-2,4-dioxo-thieno[2,3-d]pyrimidin-5-yl]carbonyl]-4-methyl-4-isoxazolidinol,
5-[[(4S)-4-Hydroxy-4-methyl-2-isoxazolidinyl]carbonyl]-3-methyl-1-(1-methylethyl)-6-[(1-phenyl-1H-pyrazol-4-yl)methyl]-thieno[2,3-d]pyrimidine-2,4-(1H,3H)-dione
6-[(8-Fluoroquinolin-4-yl)methyl]-5-{[(4S)-4-hydroxy-4-methylisoxazolidin-2-yl]carbonyl}-1-isopropyl-3-methylthieno[2,3-d]pyrimidine-2,4(1H,3H)-dione,
5-{[(4S)-4-Hydroxy-4-methylisoxazolidin-2-yl]carbonyl}-1-isopropyl-3-methyl-6-(4-pyrimidin-2-ylbenzyl)thieno[2,3-d]pyrimidine-2,4(1H,3H)-dione,
5-[[(4S)-4-Hydroxy-4-methyl-2-isoxazolidinyl]carbonyl]-3-methyl-1-(1-methylethyl)-6-[(5-(2-pyridinyl)-2-thienyl)methyl]-thieno[2,3-d]pyrimidine-2,4-(1H,3H)-dione,
6-[(1,3-Dimethyl-1H-5-pyrazolyl)methyl]-5-[[(4S)-4-hydroxy-4-methyl-2-isoxazolidinyl]carbonyl]-3-methyl-1-(1-methylethyl)-thieno[2,3-d]pyrimidine-2,4-(1H,3H)-dione,
6-[(3,5-Dimethyl-4-isothiozolyl)methyl]-5-[[(4S)-4-hydroxy-4-methyl-2-isoxazolidinyl]carbonyl]-3-methyl-1-(1-methylethyl)thieno[2,3-d]pyrimidine-2,4-(1H,3H)-dione,
5-[[(4S)-4-Hydroxy-4-methyl-2-isoxazolidinyl]carbonyl]-3-methyl-1-(1-methylethyl)-6-[[1-(2-thiazolyl)-1H-pyrazol-4-yl]methyl]thieno[2,3-d]pyrimidine-2,4-(1H,3H)-dione,
6-[(4-Fluorophenyl)methyl]-5-[[(4S)-4-hydroxy-4-methyl-2-isoxazolidinyl]carbonyl]-3-methyl-1-(1-methylethyl)thieno[2,3-d]pyrimidine-2,4-(1H,3H)-dione,
5-[[(4S)-4-Hydroxy-4-methyl-2-isoxazolidinyl]carbonyl]-3-methyl-1-(1-methylethyl)-6-(1H-1,2,3-triazol-1-ylmethyl)thieno[2,3-d]pyrimidine-2,4-(1H,3H)-dione,
6-[(6-Chloroimidazo[1,2-a]pyridin-3-yl)methyl]-5-[[(4S)-4-hydroxy-4-methyl-2-isoxazolidinyl]carbonyl]-3-methyl-1-(1-methylethyl)thieno[2,3-d]pyrimidine-2,4-(1H,3H)-dione,
5-[[(4S)-4-hydroxy-4-methylisoxazolidin-2-yl]carbonyl]-3-methyl-1-(1-methylethyl)-6-[[4-(2-pyridinyl)phenyl]methyl]-thieno[2,3-d]pyrimidine-2,4(1H,3H)-dione,
(4S)-4 Methyl-2-[[1,2,3,4-tetrahydro-3-methyl-1-(1-methylethyl)-6-[[5-methyl-1-(2-pyrimidinyl)-3-(trifluoromethyl)-1H-pyrazol-4-yl]methyl]-2,4-dioxothieno[2,3-d]pyrimidin-5-yl]carbonyl]-4-isoxazolidinol,
(4S)-2-[[6-[[3,5-Dimethyl-1-(2-pyrimidinyl)-1H-pyrazol-4yl]methyl]-1,2,3,4-tetrahydro-3-methyl-1-(1-methylethyl)-2,4-dioxothieno[2,3-d]pyrimidin-5-yl]carbonyl]-4-ethyl-4-isoxazolidinol,
(4s)-2-[[6-[[1-(2,3-Dihydro-2-oxo-4-pyrimidinyl)-3,5-dimethyl-1h-pyrazol-4-yl]methyl]-1,2,3,4-tetrahydro-3-methyl-1-(1-methylethyl)-2,4-dioxothieno[2,3-d]pyrimidin-5-yl]carbonyl]-4-methyl-4-isoxazolidinol,
5-[[(4R)-4-Hydroxy-4-methyl-2-isoxazolidinyl]carbonyl]-3-methyl-1-(1-methylethyl)-6-[[5-methyl-3-(trifluoromethyl)-1H-pyrazol-4-yl]methyl]-thieno[2,3-d]pyrimidine-2,4(1H,3H)-dione
and pharmaceutically acceptable salts thereof.

Salts for use in pharmaceutical compositions will be pharmaceutically acceptable salts, but other salts may be useful in the production of the compounds of formula I and their pharmaceutically acceptable salts. Pharmaceutically acceptable salts of the invention may, for example, include acid addition salts of the compounds of formula I as hereinbefore defined which are sufficiently basic to form such salts. Such acid addition salts include for example salts with inorganic or organic acids affording pharmaceutically acceptable anions such as with hydrogen halides (especially hydrochloric or hydrobromic acid of which hydrochloric acid is particularly preferred) or with sulphuric or phosphoric acid, or with trifluoroacetic, citric or maleic acid. Suitable salts include hydrochlorides, hydrobromides, phosphates, sulphates, hydrogen sulphates, alkylsulphonates, arylsulphonates, acetates, benzoates, citrates, maleates, fumarates, succinates, lactates and tartrates. In addition where the compounds of formula I are sufficiently acidic, pharmaceutically acceptable salts may be formed with an inorganic or organic base which affords a pharmaceutically acceptable cation. Such salts with inorganic or organic bases include for example an alkali metal salt, such as a sodium or potassium salt, an alkaline earth metal salt such as a calcium or magnesium salt, an ammonium salt or for example a salt with methylamine, dimethylamine, trimethylamine, piperidine, morpholine or tris-(2-hydroxyethyl)amine.

Preferred salts include an acid addition salt such as a hydrochloride, hydrobromide, phosphate, acetate, fumarate, maleate, tartrate, citrate, oxalate, methanesulfonate or p-toluenesulfonate, or an alkali metal salt such as a sodium or potassium salt.

Compounds of the invention can be prepared by routes analogous to those known in the art. Particular examples are given below.

In a further aspect the invention provides a process for the preparation of a compound of formula (1) which comprises:

a) when $R^3$ is a group COG, reacting a compound of the formula (10):

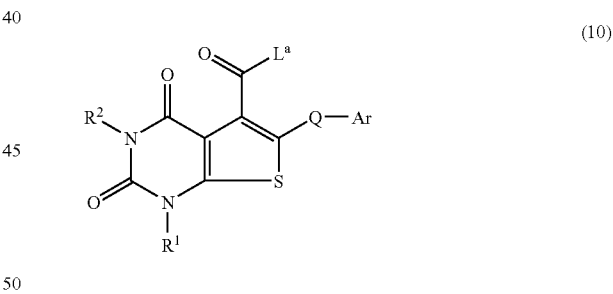

with G-H;

b) when Q is methylene, reacting a compound of the formula (11):

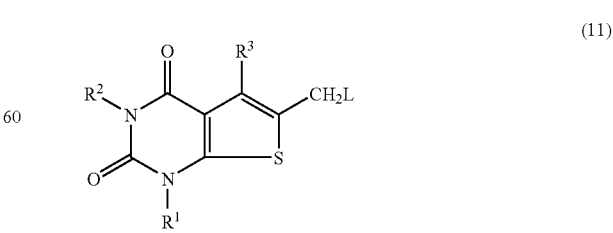

with a compound of the formula Ar—H;

c) when Q is methylene, reducing a compound of the formula (12):

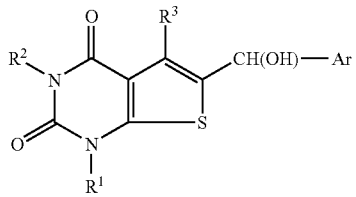

d) reacting a compound of the formula (11) or (13) to form Ar by primary ring

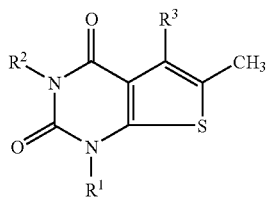

synthesis:

e) reacting a compound of the formula (14) with $R^1$-$L^2$:

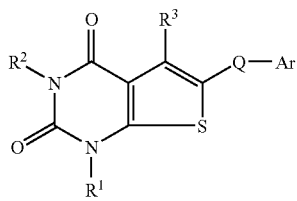

or f) when $R^3$ is $SO_2G$ reacting a compound of formula (15)

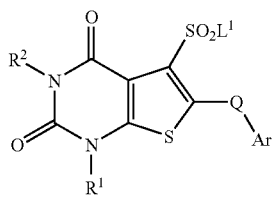

with a compound G-H

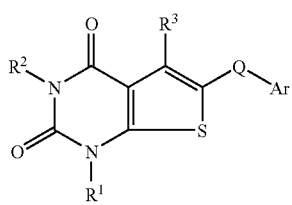

wherein $L^a$, L, $L^1$ and $L^2$ are leaving groups and $R^1$, $R^2$, $R^3$, G, Q and Ar are as defined above or are protected derivatives thereof, and optionally after a), b), c), d), e) or f) converting the compound of the formula (1) into a further compound of formula (1) and/or forming a pharmaceutically acceptable salt or solvate thereof.

In particular in the compound of formula (15), Q is methylene.

Suitable leaving groups for $L^a$, L, $L^1$ and $L^2$ would be apparent to a skilled chemist, depending upon the nature of the reaction being conducted. Examples of leaving groups may include halo, such as chloro, bromo or iodo, anhydride groups such as acetic anhydride, esters such as mesylate or tosylate, and hydroxy.

The reaction between a compound of the formula (10) and compound G-H, where G is has a nitrogen attached to the hydrogen atom shown, is conveniently carried out under amide bond forming reaction conditions, in which case, $L^a$ is hydroxy. For example, in the presence of a coupling agent such as dicyclohexylcarbodiimide or 1-ethyl-3-(3-dimethylaminopropyl)ethylcarbodiimide. Optionally a base may be used, preferably an organic base such as triethylamine. Suitable solvents are usually aprotic solvents, for example dimethylformamide or chlorinated solvents, for example dichloromethane or trichloromethane. Additionally, a compound which catalyses this type of amide bond formation reaction, such as 1-hydroxybenzotriazole, may be present. The temperature is usually in the range of about −30° C. to about 60° C., preferably at or near ambient temperature.

The reaction between a compound of the formula (11) and Ar is normally carried out in the presence of a strong base such as sodium hydride. Suitable leaving groups include halo, in particular bromo. The reaction is conveniently carried out in an inert solvent such as tetrahydrofuran, preferably at or around ambient temperature. In some circumstances, for example when Ar contains ring nitrogen atoms which do not need to be deprotonated, a milder base, such as sodium bicarbonate can be used. This reaction is conveniently used to prepare compounds in which Ar is linked through a ring nitrogen atom. However, it is possible to use this process to prepare a compound in which Ar is linked via a ring carbon atom. This can be achieved by using a strong base and a zinc salt such as zinc chloride and optionally sodium iodide as a catalyst.

A compound of formula (12) can be reduced to the corresponding methylene compound using standard reduction conditions for hydroxy groups known in the art. For example, it can be protonated with an acid such as trifluoroacetic acid and reduced with a trialkylsilane. Alternatively the hydroxy group could be converted to a stronger leaving group, such as mesylate or tosylate and the resulting compound hydrogenated in a non-hydroxylic solvent, preferably tetrahydrofuran, with a catalyst such as palladium on charcoal, in a temperature range of 0° C. to 50° C., preferably at ambient temperature and a pressure of 1 to 5 bar.

The group -Q-Ar is conveniently formed on a compound of formula (11) or (13) by primary ring-synthesis. Here, reference is made to the compendiums 'The Chemistry of Heterocyclic Compounds' E. C. Taylor and A. Weissberger (published by John Wiley and Sons) and 'Comprehensive Heterocyclic Chemistry', A. R Katritzky and C. W Rees (published by Pergamon Press (Elsevier)). For examples of the preparation of a compound of the formula (1) wherein Ar is 3,5-dimethylpyrazol-4-yl or 1,3,5-trimethylpyrazol-4-yl see examples 11 and 12 in the specific examples.

A compound of the formula (14) may be reacted with a compound of formula $R^1$-$L^2$ in the presence of a mild base, such as potassium carbonate, in a dipolar aprotic solvent such as DMF, in a temperature range of ambient temperature to 170° C.

Particular examples of $L^1$ is formula (15) is chlorine.

A compound of the formula (1) may be prepared from another compound of formula (1) by chemical modification.

For example a compound of the formula (1) wherein Q is methylene can be oxidised to a compound of the formula (1) wherein Q is carbonyl. A preferred oxidising agent is 2,3-dichloro-5,6-dicyano-1,4-benzoquinone (DDQ) in an inert organic solvent such as tetrahydrofuran. In some circumstances oxidation can be effected by exposure of the methylene compound to air.

Alternatively or additionally, compounds of formula (1) where Ar is a group of sub-formula (i) above, wherein $R^{12}$ is hydrogen can be converted to compounds of formula (i) where $R^{12}$ is other than hydrogen by reaction with a compound of formula (XV)

where $R^{12'}$ is a group $R^{12}$ other than hydrogen, and L" is a leaving group such as halo, and in particular bromo. Such a reaction may be carried out in an organic solvent such as acetonitrile or dioxan. If necessary the reaction can be carried out in the presence of a base such as an alkali metal carbonate, for instance potassium carbonate, and in the presence of a catalyst such as a copper salt like copper iodide. Also if necessary, the reaction can be effected under an inert atmosphere such as nitrogen.

Intermediates of the formulae (10) may be formed from a compound of the formula (16):

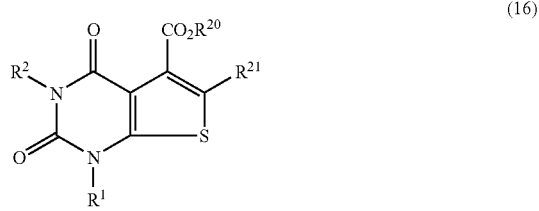

wherein $R^{20}$ is $C_{1-6}$alkyl, for example methyl or ethyl, and $R^{21}$ is either —$CH_2L$ (wherein L is as hereinabove defined) or —CH(OH)Ar.

A compound of formula (16) wherein $R^{21}$ is —$CH_2L$ may be reacted with Ar under similar conditions to those described for process b) above.

When Ar is linked via a ring carbon atom, a compound of formula (15) wherein $R^{21}$ is —CH(OH)Ar may be reduced using similar conditions to those described for process c) above.

A compound of the formula (12) or (16) wherein $R^{21}$ is —CH(OH)Ar may be formed by reacting a compound of the formula (17):

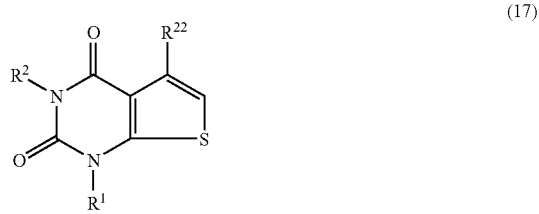

(wherein $R^{22}$ is $R^3$ or —$CO_2R^{20}$, as appropriate) with a compound of formula Ar—CHO in the presence of a strong base such as a lithium dialkylamide, for example, lithium diisopropylamide, in an inert organic solvent such as tetrahydrofuran and initially at a low temperature, such as –78° C. and subsequently allowing it to warm to ambient temperature.

The intermediates are in general prepared from a compound of the formula (18):

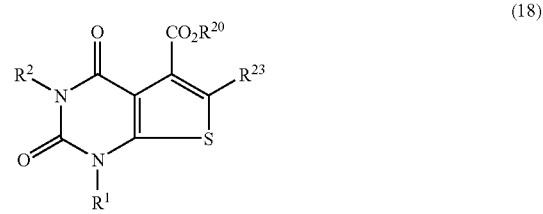

wherein $R^{23}$ is hydrogen or methyl.

When $R^{21}$ is —CH(OH)Ar, $R^{23}$ is hydrogen and the compound of formula (17) may be reacted with Ar—CHO as described above for the compound of formula (16).

When $R^{21}$ is —$CH_2L$, $R^{23}$ is methyl which is converted to —$CH_2L$ by for example halogenation. When L is bromo, the methyl group may be brominated using a standard brominating agent such as N-bromosuccinimide under standard conditions.

A compound of formula (18) wherein $R^{23}$ is hydrogen may be formed by firstly reacting a compound of formula (19):

with an alkylbromopyruvate, such as ethylbromopyruvate, in the presence of a mild base such as an alkali carbonate, for example potassium carbonate in a polar solvent e.g. DMF at a temperature between 5° C. and 50° C. and then secondly treating the resulting adduct with a Lewis acid preferably titanium tetrachloride, in an inert solvent e.g. dichloromethane at a temperature between –20° C. and 50° C., preferably between 0° C. and 25° C.

A compound of formula (18) wherein $R^{23}$ is methyl may be formed by firstly reacting a compound of formula (19) with an alkyl 3-bromo-2-oxobutanoate such as methyl 3-bromo-2-oxobutanoate in the presence of a mild base such as an alkali carboxylate, for example sodium acetate in a polar solvent such as DMF, or preferably water, at a temperature between 5° C. and 50° C. and then secondly treating the resulting adduct with a Lewis acid, preferably titanium tetrachloride, in an inert solvent e.g. dichloromethane at a temperature between –20° C. and 50° C., preferably between 0° C. and 25° C.

A compound of formula (18) may be formed by reacting a compound of formula (20):

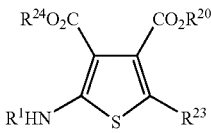
(20)

(wherein $R^{24}$ is $C_{1\text{-}4}$alkyl, for example ethyl)

with acetyl cyanate in an inert solvent, for example toluene, at a temperature of from 0° C. to 50° C., and then treating the product of that conversion with a solution of a metal alkoxide in the alkanol (eg sodium methoxide in methanol) at a temperature of from 0° C. to 30° C., in the presence of a compound of formula $R^2$-$L^1$ (wherein $L^1$ is a leaving group, eg iodide).

A compound of formula (20) may be prepared by the reaction of a compound of formula (20): $R^1$—N=C=S with a Wittig compound, for example a compound of the formula (22):

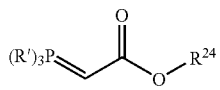
(22)

(wherein R' is phenyl or substituted phenyl such as tolyl)

in an inert solvent, for example THF, at a temperature of from 20° C. to 80° C., and treatment of the resulting adduct in situ with a compound of formula (23):

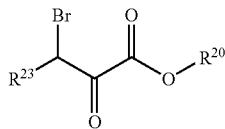
(23)

at a temperature of from −78° C. to 60° C.

A compound of formula (19) may be formed by reacting a compound of formula (24):

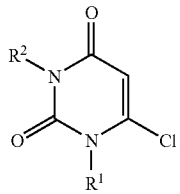
(24)

with an alkaline metal thiol, such as sodium thiol, in a polar solvent, such as an alcohol, for example ethanol, in a temperature range of 10° C. to 50° C.

A compound of formula (23) may be formed by reacting a compound of formula (25):

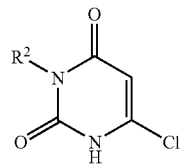
(25)

with a compound of formula $R^1$-$L^2$ under conditions described for process e) above.

A compound of formula (15) can be prepared by reacting a compound of formula (26):

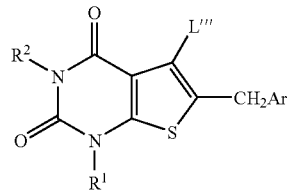
(26)

wherein L''' is a leaving group, and in particular a halo group such as bromo, with a Grignard reagent followed by addition of $SO_2$, oxidation and chlorination The reaction is carried out in a suitable solvent such as THF at a temperature of −70° C. to 30° C., preferably at −20° C. to 20° C. The resulting sulphinic acid can be oxidised to the corresponding sulphonic acid and chlorinated, for example using $PCl_5$.

Compounds of formula (26) are prepared by treating the corresponding halo derivative, such as the bromo derivative, with a strong base such as lithium diisopropylamide at reduced temperature followed by treatment with a compound ArCHO. The reaction is suitable carried out in THF at a temperature of −70° C. to 30° C., preferably at −50° C. to 0° C.

The precusor halo compounds are prepared by halogenation, and in particular bromination, of a compound of formula (27):

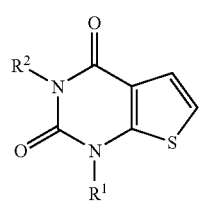
(27)

The reaction can be carried out using for instance, bromine in chloroform at a temperature of from −10° C. to 60° C., preferably at about ambient temperature.

Starting materials as defined above are available commercially or can be prepared using routine chemistry known in the art.

The compounds of formula (1) above may be converted to a pharmaceutically acceptable salt or solvate thereof.

Certain compounds of formula (1) are capable of existing in stereoisomeric forms. It will be understood that the invention encompasses all geometric and optical isomers of the compounds of formula (1) and mixtures thereof including racemates. These also form an aspect of the present invention.

Isomers may be resolved or separated by conventional techniques, e.g. chromatography or fractional crystallisation. Enantiomers may be isolated by separation of a racemic or other mixture of the compounds using conventional techniques (e.g. chiral High Performance Liquid Chromatography (HPLC)). Alternatively the desired optical isomers may be made by reaction of the appropriate optically active starting materials under conditions which will not cause racemisation, or by derivatisation, for example with a homochiral acid followed by separation of the diastereomeric derivatives by conventional means (e.g. HPLC, chromatography over silica) or may be made with achiral starting materials and chiral reagents. All stereoisomers are included within the scope of the invention.

The compounds of the invention may be isolated from their reaction mixtures using conventional techniques.

The compounds of the invention are useful because they possess pharmacological activity in human and non-human animals. They are indicated as pharmaceuticals for use in the (prophylactic) treatment of autoimmune, inflammatory, proliferative and hyperproliferative diseases and immunologically mediated diseases including rejection of transplanted organs or tissues and Acquired Immunodeficiency Syndrome (AIDS).

Examples of these conditions are:
(1) (the respiratory tract) airways diseases including chronic obstructive pulmonary disease (COPD); asthma, such as bronchial, allergic, intrinsic, extrinsic and dust asthma, particularly chronic or inveterate asthma (e.g. late asthma and airways hyper-responsiveness); bronchitis; acute, allergic, atrophic rhinitis and chronic rhinitis including rhinitis caseosa, hypertrophic rhinitis, rhinitis purulenta, rhinitis sicca and rhinitis medicamentosa; membranous rhinitis including croupous, fibrinous and pseudomembranous rhinitis and scrofoulous rhinitis; seasonal rhinitis including rhinitis nervosa (hay fever) and vasomotor rhinitis; sarcoidosis, farmer's lung and related diseases, fibroid lung and idiopathic interstitial pneumonia;
(2) (bone and joints) rheumatoid arthritis, seronegative spondyloarthropathies (including ankylosing spondylitis, psoriatic arthritis and Reiter's disease), Behcet's disease, Sjogren's syndrome and systemic sclerosis;
(3) (skin) psoriasis, atopical dermatitis, contact dermatitis and other eczmatous dermitides, seborrhoetic dermatitis, Lichen planus, Pemphigus, bullous Pemphigus, Epidermolysis bullosa, urticaria, angiodermas, vasculitides, erythemas, cutaneous eosinophilias, uveitis, Alopecia areata and vernal conjunctivitis;
(4) (gastrointestinal tract) Coeliac disease, proctitis, eosinopilic gastro-enteritis, mastocytosis, Crohn's disease, ulcerative colitis, food-related allergies which have effects remote from the gut, e.g., migraine, rhinitis and eczema;
(5) (other tissues and systemic disease) multiple sclerosis, atherosclerosis, Acquired Immunodeficiency Syndrome (AIDS), lupus erythematosus, systemic lupus, erythematosus, Hashimoto's thyroiditis, myasthenia gravis, type I diabetes, nephrotic syndrome, eosinophilia fascitis, hyper IgE syndrome, lepromatous leprosy, sezary syndrome and idiopathic thrombocytopenia pupura;
(6) (allograft rejection) acute and chronic following, for example, transplantation of kidney, heart, liver, lung, bone marrow, skin and cornea; and chronic graft versus host disease; and
(7) cancer.

Accordingly, the present invention provides a compound of formula (1) or a pharmaceutically acceptable salt thereof as hereinbefore defined for use in therapy.

In another aspect, the invention provides the use of a compound of formula (1) or a pharmaceutically acceptable salt thereof as hereinbefore defined in the manufacture of a medicament for use in therapy.

In the context of the present specification, the term "therapy" also includes "prophylaxis" unless there are specific indications to the contrary. The terms "therapeutic" and "therapeutically" should be construed accordingly.

Prophylaxis is expected to be particularly relevant to the treatment of persons who have suffered a previous episode of, or are otherwise considered to be at increased risk of, the disease or condition in question. Persons at risk of developing a particular disease or condition generally include those having a family history of the disease or condition, or those who have been identified by genetic testing or screening to be particularly susceptible to developing the disease or condition.

The invention further provides a method of effecting immunosuppression (e.g. in the treatment of allograft rejection) which comprises administering to a patient a therapeutically effective amount of a compound of formula (1) or a pharmaceutically acceptable salt thereof as hereinbefore defined.

The invention still further provides a method of treating, or reducing the risk of, an airways disease (e.g. asthma or COPD) in a patient suffering from, or at risk of, said disease, which comprises administering to the patient a therapeutically effective amount of a compound of formula (1) or a pharmaceutically acceptable salt thereof as hereinbefore defined.

For the above-mentioned therapeutic uses the dosage administered will, of course, vary with the compound employed, the mode of administration, the treatment desired and the disorder indicated. However, in general, for effecting immunosuppression, the daily dosage of the compound of formula (1) will be in the range from 0.1 mg/kg, preferably from 0.3 mg/kg, more preferably from 0.5 mg/kg and still more preferably from 1 mg/kg up to and including 30 mg/kg. For the treatment of airways diseases, the daily dosage of the compound of formula (1) will typically be in the range from 0.001 mg/kg to 30 mg/kg.

The compounds of formula (1) and pharmaceutically acceptable salts thereof may be used on their own but will generally be administered in the form of a pharmaceutical composition in which the formula (1) compound/salt/solvate (active ingredient) is in association with a pharmaceutically acceptable adjuvant, diluent or carrier. Depending on the mode of administration, the pharmaceutical composition will preferably comprise from 0.05 to 99% w (per cent by weight), more preferably less than 80% w, e.g. from 0.10 to 70% w, and even more preferably less than 50% w, of active ingredient, all percentages by weight being based on total composition.

Thus, the present invention also provides a pharmaceutical composition comprising a compound of formula (1) or a pharmaceutically acceptable salt thereof as hereinbefore defined, in association with a pharmaceutically acceptable adjuvant, diluent or carrier.

The invention further provides a process for the preparation of a pharmaceutical composition of the invention which comprises mixing a compound of formula (1) or a pharmaceutically acceptable salt thereof as hereinbefore defined, with a pharmaceutically acceptable adjuvant, diluent or carrier.

The pharmaceutical composition of the invention may be administered topically (e.g. to the lung and/or airways or to the skin) in the form of solutions, suspensions, heptafluoroalkane aerosols and dry powder formulations; or systemically, e.g. by oral administration in the form of tablets, capsules, syrups, powders or granules, or by parenteral administration in the form of solutions or suspensions, or by subcutaneous administration or by rectal administration in the form of suppositories or transdermally.

The ability of compounds which can inhibit PMA/ionomycin-stimulated peripheral blood mononuclear cell proliferation can be assessed, for example using the procedure set out below:

The invention will now be illustrated in the following Examples in which, unless otherwise stated:

(i) evaporations were carried out by rotary evaporation in vacuo and work-up procedures were carried out after removal of residual solids such as drying agents by filtration;

(ii) operations were carried out at ambient temperature, that is in the range 18-25° C. and under an atmosphere of an inert gas such as argon or nitrogen;

(iii) yields are given for illustration only and are not necessarily the maximum attainable;

(iv) the structures of the end-products of the formula I were confirmed by nuclear (generally proton) magnetic resonance (NMR) and mass spectral techniques; proton magnetic resonance chemical shift values were measured on the delta scale and peak multiplicities are shown as follows: s, singlet; d, doublet; t, triplet; m, multiplet; br, is broad; q, quartet, quin, quintet;

(v) intermediates were not generally fully characterised and purity was assessed by thin layer chromatography (TLC), high-performance liquid chromatography (HPLC), mass spectrometry (MS), infra-red (IR) or NMR analysis;

Abbreviations

| | |
|---|---|
| 2,3-Dichloro-5,6-dicyano-1,4-benzoquinone | DDQ |
| Dimethylformamide | DMF |
| Tetrahydrofuran | THF |

The following examples illustrate the invention.

EXAMPLE 1

(S)-2-[[6-[(3,5-Dimethyl-1H-pyrazol-4-yl)methyl]-1, 2,3,4-tetrahydro-3-methyl-1-(2-methylpropyl)-2,4-dioxo-thieno[2,3-d]pyrimidin-5-yl]carbonyl]-4-methyl-4-isoxazolidinol

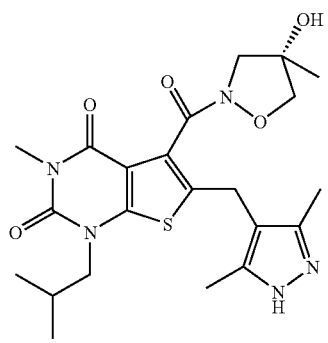

a) 2-[[(2S)-2-Methyloxiranyl]methoxy]-1H-isoindole-1,3(2H)-dione

A mixture of N-hydroxypthalimide (5.3 g), [(2S)-2-methyloxiran-2-yl]methyl 3-nitrobenzenesulfonate (5.9 g) and triethylamine (10.6 ml) in dichloromethane (15 ml) was stirred under nitrogen at ambient temperature for 24 hours.

The reaction mixture was poured onto a silica column and eluted with dichloromethane to give the sub-title compound as a white solid (3.1 g).

MS (APCI) 234 [M+H]$^+$ $\delta^1 H_{CDCl_3}$ 1.63 (3H, s), 2.69 (1H, d), 2.76 (1H, d), 4.17 (1H, d), 4.21 (1H, d), 7.73-7.78 (2H, m), 7.82-7.87 (2H, m)

b) 2-[[(2R)-3-Chloro-2-hydroxy-2-methylpropyl] oxy]-1H-isoindole-1,3(2H)-dione

The product of part a) (3.0 g) was treated with concentrated hydrochloric acid (12 ml) and stirred at ambient temperature for 2 hours.

The mixture was partitioned between water and dichloromethane, the organics were dried and purified by chromatography (EtOAc) to give the sub-title compound as a white solid (3.3 g).

$\delta^1 H_{DMSO}$ 1.29(3H, S), 3.67 (1H, d), 3.76 (1H, d), 4.09 (1H, d), 4.15 (1H, d), 7.86 (4H, s), 5.24 (1H,s)

c) 2-[[(4S)-4-Hydroxy-4-methyl-2-isoxazolidinyl] carbonyl]-benzoic acid methyl ester Prepared from a solution of the product of part b) (3.3. g) in methanol (25 ml) which was treated with triethylamine (3.4 ml) and heated under nitrogen at reflux for 1 hour. The mixture was concentrated to dryness and purified by chromatography eluting with a gradient from dichloromethane to 5% methanol in dichloromethane. The chiral purity of the product was enhanced by recrystallising twice from acetonitrile to give the sub-title compound as a white solid (1.92 g).

HPLC: (9010THIP.M) 50 mm chiracel AD column, ee>99% $\delta^1 H_{CDCl_3}$ 1.52 (3H, s), 3.59 (1H, d), 3.81 (1H, d), 3.88 (1H, d), 4.04 (1H, s), 4.34 (1H, d), 3.92 (3H, s), 7.45 (1H, d), 7.49 (1H, t), 7.62 (1H, t), 8.00 (1H, d).

d) (4S)-4-Methyl-4-isoxazolidinol hydrochloride

Prepared from a solution of the product of part c) (4.9 g) in 2N hydrochloric acid (30 ml) which was heated under nitrogen at reflux for 4 hours. After cooling the precipitate was removed by filtration and the liquors concentrated to dryness under vacuo. The residue was triturated with acetonitrile to give the sub-title compound as a white solid (1.79 g).

$\delta^1H_{DMSO}$ 1.42 (3H, s), 3.29 (1H, d), 3.41 (1H, dD), 3.87 (1H, d), 4.05 (1H, dd).

e) 6-[(3,5-Dimethyl-1H-pyrazol-4-yl)methyl]-1,2,3,4-tetrahydro-3-methyl-1-(2-methylpropyl)-2,4-dioxo-thieno[2,3-d]pyrimidine-5-carboxylic acid methyl ester To a solution of 6-(bromomethyl)-1,2,3,4-tetrahydro-3-methyl-1-(2-methylpropyl)-2,4-dioxo-thieno[2,3-d]pyrimidine-5-carboxylic acid methyl ester (1.0 g)in chloroform (25 ml) was added zinc acetylacetonate hydrate (0.73 g) and the mixture heated at reflux for 30 minutes. After cooling the mixture was stirred vigorously with saturated sodium bicarbonate, the organics were then collected and treated with 35% aqueous hydrazine (1.0 ml) and stirred at ambient temperature for 16 hours, The reaction mixture was washed with water and purified by chromatography (ethyl acetate) to afford the sub-title compound as a white solid (1.04 g).

$\delta^1H_{CDCl3}$ 0.93 (6H, d), 2.21-2.26 (1H, m), 2.21 (6H, s), 3.39 (3H, s), 3.68 (2H, d), 3.90 (2H, s), 3.96 (3H, s).

f) 6-[(3,5-Dimethyl-1H-pyrazol-4-yl)methyl]-1,2,3,4-tetrahydro-3-methyl-1-(2-methylpropyl)-2,4-dioxo-thieno[2,3-d]pyrimidine-5-carboxylic acid monosodium salt Prepared from a solution of the product of step e) (19.0 g) and sodium hydroxide (2.52 g) in THF (400 ml), water (35 ml) and methanol (60 ml). After stirring at ambient temperature for 24 hours the precipitate was filtered off and washed with cold THF to give the sub-title compound as a white solid (17.2 g).

$\delta^1H_{D2O}$ 0.90 (6H, d), 2.18 (6H, s), 2.20 (1H, non), 3.34 (3H, s), 3.72-3.77 (2H, d), 3.89 (2H, s).

g) (4S)-2-[[6-[(3,5-Dimethyl-1H-pyrazol-4-yl)methyl]-1,2,3,4-tetrahydro-3-methyl-1-(2-methylpropyl)-2,4-dioxo-thieno[2,3-d]pyrimidin-5-yl]carbonyl]-4-methyl-4-isoxazolidinol A suspension of the product of step f) (200 mg), the product of step d) (81 mg) and Pybrop (332 mg) in dichloromethane (10 ml) was treated with triethylamine (0.20 ml) and the mixture stirred at ambient temperature for 16 hours.

The reaction mixture was then purified by both normal phase (0% to 10% methanol in dichloromethane) and reverse phase (5% to 95% methanol in 0.1% aqueous ammonium acetate) chromatography to give the title compound as a white solid (90 mg).

$\delta^1H_{DMSO}$ 130° C., 0.90 (6H, d), 1.41 (3H, s), 2.08 (6H, s), 2.18 (1H, non), 3.23 (3H, s), 3.67 (2H, d), 3.59-3.72 (3H, m), 3.77-3.82 (1H,m), 3.78 (2H, s), 4.92 (1H, s), 11.67 (1H, s).

EXAMPLE 2

(S)-2-[[6-[(3,5-Dimethyl-1H-pyrazol-4-yl)methyl]-1,2,3,4-tetrahydro-3-methyl-1-(2-methylethyl)-2,4-dioxo-thieno[2,3-d]pyrimidin-5-yl]carbonyl]-4-methyl-4-isoxazolidinol

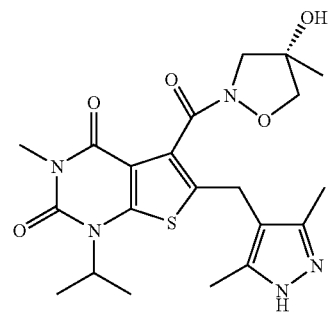

a) 6-[(3,5-Dimethyl-1H-pyrazol-4-yl)methyl]-1,2,3,4-tetrahydro-3-methyl-1-(2-methylethyl)-2,4dioxo-thieno[2,3-d]pyrimidine-5-carboxylic acid methyl ester Prepared as example 1 step e) using 6-(bromomethyl)-1,2,3,4-tetrahydro-3-methyl-1-(2-methylethyl)-2,4-dioxo-thieno[2,3-d]pyrimidine-5-carboxylic acid methyl ester.

$\delta^1H_{CDCl3}$ 1.53 (6H, d), 2.21 (6H, s), 3.36 (3H, s), 3.89 (2H, s), 3.96 (3H, s), 4.47 (1H,s).

b) 6-[(3,5-Dimethyl-1H-pyrazol-4-yl)methyl-]1,2,3,4-tetrahydro-3-methyl-1-(2-methylethyl)-2,4-dioxo-thieno[2,3-d]pyrimidine-5-carboxylic acid monosodium salt Prepared using the method of example 1 step f) and the product of step a).

$\delta^1H_{DMSO}$ 1.44 (6H, d), 2.10 (6H, s), 3.17 (3H, s), 3.72 (2H, s), 4.32 (1H, s).

c) (4S)-2-[[6-[(3,5-Dimethyl-1H-pyrazol-4-yl)methyl]-1,2,3,4-tetrahydro-3-methyl-1-(2-methylethyl)-2,4-dioxo-thieno[2,3-d]pyrimidin-5-yl]carbonyl]-4-methyl-4-isoxazolidinol Prepared using the method of example 1 step g) using the product of step b and example 1 step d).

$\delta^1H_{DMSO}$ 130° C., 1.41 (3H, s), 1.46 (6H, d), 2.09 (6H, s), 3.20 (3H, s), 3.60-3.72 (3H, m), 3.78-3.82 (1H,m), 3.77 (2H, s), 4.46 (1H, sep), 4.94 (1H, s), 11.71 (1H, s).

EXAMPLE 3

1-Cyclopropyl-6-[(3,5-dimethyl-1H-pyrazol-4-yl)methyl]-5-[[(4S)-4-hydroxy-4-methyl-2-isoxazolidinyl]carbonyl]-3-methyl-thieno[2,3-d]pyrimidine-2,4(1H,3H)-dione

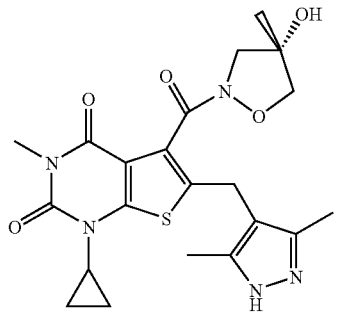

a) 2-(Cyclopropylamino)-5-methyl-3,4-thiophenedicarboxylic acid, 3-ethyl 4-methyl ester To a solution of (triphenylphosphoranylidene)-acetic acid ethyl ester (15 g) in anhydrous tetrahydrofuran (100 ml) was added isothiocyanato-cyclopropane (4.4 g) and the mixture was refluxed under a nitrogen atmosphere for 20 hr. After allowing to cool to ambient temperature the reaction mixture was cooled to −78° C. and then a solution of 3-bromo-2-oxo-butanoic acid methyl ester (8.7 g) in anhydrous tetrahydrofuran (10 ml) was added. The resulting mixture was allowed to warm to ambient temperature and then refluxed for 20 hr., then ambient temperature for 2 days. The reaction was poured into water and extracted with diethyl ether. The collected organic extract was dried over magnesium sulfate, filtered and evaporated under reduced pressure. The residue was purified by column chromatography over silica, eluting with i-hexane/ethyl acetate (95:5) then triturated with i-hexane/diethyl ether (8:2) to give the sub-title compound as a solid (7.5 g).

$^1H_{CDCl3}$ 0.66 (2H, m), 0.75 (2H, m), 1.26 (3H, t), 2.27 (3H, s), 2.56 (1H, m), 3.83 (3H, s), 4.08 (2H, quartet), 7.55 (1H, bs)

b) 1-Cyclopropyl-1,2,3,4-tetrahydro-6-methyl-2,4-dioxo-thieno-[2,3-d]pyrimidine-5-carboxylic acid, methyl ester To a suspension of silver isocyanate (4.4 g) in anhydrous toluene (30 ml) was added acetyl chloride (1.8 ml) dropwise over 5 min. and the resulting mixture was stirred under a nitrogen atmosphere at ambient temperature for 35 min. A solution of the product of part a) (7.5 g) in anhydrous toluene (5 ml) was then added and the mixture was stirred for 20 hr. at ambient temperature. The reaction was diluted with diethyl ether and the precipitate was filtered. The resulting filtrate was washed with sodium bicarbonate solution, dried over magnesium sulfate, filtered and evaporated under reduced pressure. The resulting oil (9 g) was treated with sodium methoxide solution (21 ml of a 25 wt % solution in methanol) and the reaction was stirred under a nitrogen atmosphere for 20 hr. The mixture was evaporated under reduced pressure and the resulting oil was partitioned between ethyl acetate and water. The water layer was separated and filtered to give the sub-title compound as a solid (3.16 g).

MS (ESI) 281 [M+H]$^+$ $^1H_{DMSO}$ 0.96 (2H, m), 1.06 (2H, m), 2.38 (3H, s), 3.01 (1H, m), 3.78 (3H, s), 11.26 (1H, bs)

c) 1-Cyclopropyl-1,2,3,4-tetrahydro-3,6-dimethyl-2,4-dioxo-thieno[2,3-d]pyrimidine-5-carboxylic acid, methyl ester To a solution of the product of part b) (3.15 g) in anhydrous dimethylformamide (40 ml) was added potassium carbonate (1.9 g) and methyl iodide (0.84 ml). The mixture was stirred under a nitrogen atmosphere at ambient temperature for 3 days. The mixture was poured into water and the resulting solid was collected by filtration to give the sub-title compound as a solid (2.8 g).

MS (ESI) 295 [M+H]$^+$ $^1H_{DMSO}$ 1.01 (2H, m), 1.05 (2H, m), 2.39 (3H, s), 3.07 (1H, m), 3.18 (3H, s), 3.80 (3H, s)

d) 6-(Bromomethyl)-1-cyclopropyl-1,2,3,4-tetrahydro-3-methyl-2,4-dioxo-thieno[2,3-d]pyrimidine-5-carboxylic acid, methyl ester To a suspension of the product of part c) (2.8 g) in ethyl acetate (50 ml) was added N-bromosuccinimide (1.9 g) and azobis-isobutyronitrile (0.1 g). The resulting mixture was refluxed under a nitrogen atmosphere for 2 hr. then allowed to cool. This mixture was washed successively with cold 0.5M sodium hydroxide solution then water, dried over magnesium sulfate, filtered and evaporated under reduced pressure. The resulting solid was triturated from cold diethyl ether to give the sub-title compound as a solid (2.8 g).

$^1H_{CDCl3}$ 1.10 (2H, m), 1.24 (2H, m), 3.03 (1H, m), 3.37 (3H, s), 3.99 (3H, s), 4.68 (2H, s)

e) 1-Cyclopropyl-6-[(3,5-dimethyl-1H-pyrazol-4-yl)methyl]-1,2,3,4-tetrahydro-3-methyl-2,4-dioxo-thieno[2,3-d]pyrimidine-5-carboxylic acid, methyl ester Prepared from the product of part d) following the procedure of example 1, part e) to give the sub-title compound as a solid.

MS (ESI) 389 [M+H]$^+$ $^1H_{DMSO}$ 0.93 (2H, m), 1.04 (2H, m), 2.07 (6H, m), 3.02 (1H, m), 3.17 (3H, s), 3.78 (3H, s), 3.81 (2H, s), 12.12 (1H, bs)

f) 1-Cyclopropyl-6-[(3,5-dimethyl-1H-pyrazol)-4-yl)methyl]-1,2,3,4-tetrahydro-3-methyl-2,4-dioxo-thieno[2,3-d]pyrimidine-5-carboxylic acid, monosodium salt Prepared from the product of part e) following the procedure of example 1, part f) to give the sub-title compound as a solid.

MS (ESI) 375 [M+H]$^+$ $^1H_{DMSO}$ 0.84 (2H, m), 1.02 (2H, m), 2.06 (6H, s), 2.94 (1H, m), 3.17 (3H, s), 3.75 (2H, s), 11.98 (1H, bs)

g) 1-Cyclopropyl-6-[(3,5-dimethyl-1H-pyrazol-4-yl)methyl]-5-[[(4S)-4-hydroxy-4-methyl-2-isoxazolidinyl]carbonyl]-3-methyl-thieno[2,3-d]pyrimidine-2,4(1H,3H)-dione Prepared from the product of part f) following the procedure of example 1, part g) to give the title compound as a solid.

MS (ESI) 460 [M+H]+ $^1H_{DMSO}$ 0.93 (2H, m), 1.03 (2H, m), 1.37-1.42 (3H, m), 2.08 (6H, bs), 3.02 (1H, m), 3.15 (3H, m), 3.58-3.80 (6H, m), 5.41 (1H, br s)

EXAMPLE 4

(S)-2-[[6-[(1H-1,2,3-Benzotriazol-1-yl)methyl]-1,2,3,4-tetrahydro-3-methyl-1-(1-methylethyl)-2,4-dioxo-thieno[2,3-d]pyrimidin-5-yl]carbonyl]-4-methyl-4-isoxazolidinol

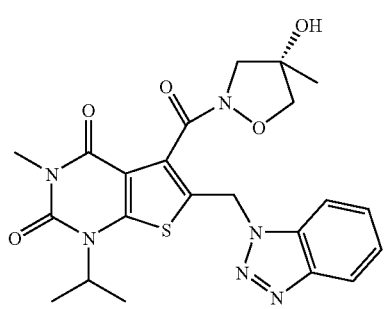

Prepared by the method of example 1 part g using 6-[(1H-1,2,3-Benzotriazol-1-yl)methyl]-1,2,3,4-tetrahydro-3-methyl-1-(1-methylethyl)-2,4-dioxo-thieno[2,3-d]pyrimidine-5-carboxylic acid (0.15 g) to give a foam (0.042 g).

$^1H_{CDCl3}$ 1.51 (9H, m inc H$_2$O), 3.34 (3H, s), 3.37 (1H, d), 3.82 (1H, d), 3.97 (1H, d), 4.52 (1H, bm), 4.54 (1H, d), 5.34 (1H,s), 6.00 (2H, dd), 7.38 (1H, t), 7.49 (1H, t).

EXAMPLE 5

(S)-2-[[6-[(4,5-Dichloro-2-methyl-1H-imidazol-1-yl)methyl]-1,2,3,4-tetrahydro-1-ethyl-3-methyl-2,4-dioxo-thieno[2,3-d]pyrimidin-5yl]carbonyl]-4-methyl-4-isoxazolidinol

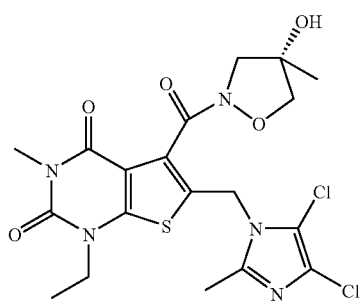

Prepared by the method of example 1 part g using 6-[(4,5-dichloro-2-methyl-1H-imidazol-1-yl)methyl]-1,2,3,4-tetrahydro-1-ethyl-3-methyl)-2,4-dioxo-thieno[2,3-d]pyrimidine-5-carboxylic acid to give the title compound (0.094 g) mp 130-133 C $^1H_{CDCl3}$ 1.38 (3H, t), 1.52 (3H, s), 2.40 (3H, s), 3.39 (3H, s), 3.43 (1H, d), 3.38 (1H, d), 3.96 (1H, d), 4.00 (2H, m), 4.46 (1H, d), 5.23 (2H, dd), 5.27 (1H, s).

EXAMPLE 6

5-[[(4S)-4-Hydroxy-4-methyl-2-isoxazolidinyl]carbonyl]-3-methyl-1-(2-methylpropyl)-6-(1H-pyrrolo[2,3-b]pyridin-3-ylmethyl)thieno[2,3-d]pyrimidine-2,4-(1H,3H)-dione

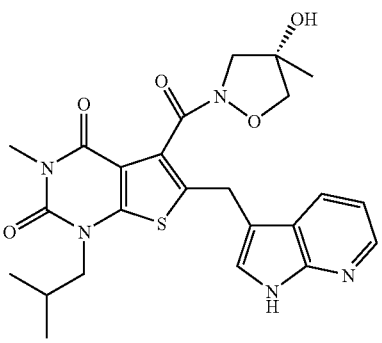

a) 1,2,3,4-Tetrahydro-3-methyl-1-(2-methylpropyl)-2,4-dioxo-6-(1H-pyrrolo[2,3-b]pyridin-3-ylmethyl)thieno[2,3-d]pyrimidine-5-carboxylic acid methyl ester To a solution of 7-azaindole (0.78 g) in anhydrous THF (30 ml) was added 2.5M n-BuLi in hexanes (2.6 ml) dropwise at 10° C. under nitrogen. After stirring the mixture for 15 mins 1.0M zinc chloride in ether (6.61 ml) was added and the mixture stirred at room temperature for 2 hr. The solvent was removed in vacuo and the residue diluted with anhydrous toluene (20 ml) then a solution of 6-(bromomethyl)-1,2,3,4-tetrahydro-3-methyl-1-(2-methylpropyl)-2,4-dioxo-thieno[2,3-d]pyrimidine-5-carboxylic acid methyl ester (2.0 g) in anhydrous toluene (10 ml) and a catalytic amount of potassium iodide were added and the reaction mixture stirred under nitrogen for 48 hr. The solvent was decanted, diluted with water and extracted with ethyl acetate, the organic extracts washed with water, dried over anhydrous magnesium sulfate, filtered and evaporated under reduced pressure. The residue was purified by column chromatography over silica, eluting with i-hexane/ethyl acetate (1:1) to give the sub-title compound (1.37 g).

MS (ESI) 427 [M+H]+ b) 1,2,3,4-Tetrahydro-3-methyl-1-(2-methylpropyl)-2,4-dioxo-6-(1H-pyrrolo[2,3-b]pyridin-3-ylmethyl)thieno[2,3-d]pyrimidine-5-carboxylic acid To a solution of the product of part a) in THF (15 ml) and methanol (7.5 ml) was added 1N sodium hydroxide (7.5 ml) and the mixture stirred under nitrogen for 18 hr. It was acidified with 2.5N hydrochloric acid and extracted with dichloromethane, the organic extracts were washed with water, dried over anhydrous magnesium sulfate, filtered and evaporated under reduced pressure to give the sub-title compound as a solid (1.22 g)

MS (ESI) 413 [M+H]+ c) 5-[[(4S)-4-Hydroxy-4-methyl-2-isoxazolidinyl]carbonyl]-3-methyl-1-(2-methylpropyl)-6-(1H-pyrrolo[2,3-b]pyridin-3-ylmethyl)thieno[2,3-d]pyrimidine-2,4-(1H,3H)-dione Prepared from the product of part b) by the method of example 1 part g) to give the title compound as a solid.

MS (APCI) 427 [M+H]+ $^1H_{DMSO}$ 0.82-0.85 (6H, m), 1.33-1.45 (3H, m), 2.04-2.12 (1H, m), 3.16-3.20 (3H, m), 3.37-3.99 (6H, m), 4.13-4.23 (2H, m), 5.45-5.48 (1H, m)<6.99-7.02 (1H, m), 7.42-7.43 (1H, m), 7.91-7.96 (1H, m), 8.18-8.19 (1H, m), 11.52-11.55 (1H, m)

EXAMPLE 7

(4S)-4-methyl-2-[[1,2,3,4-tetrahydro-3-methyl-2,4-dioxo-1-propyl-6-(4-quinolinylmethyl)thieno[2,3-d]pyrimidin-5-yl]carbonyl]-4-isoxazolidinol

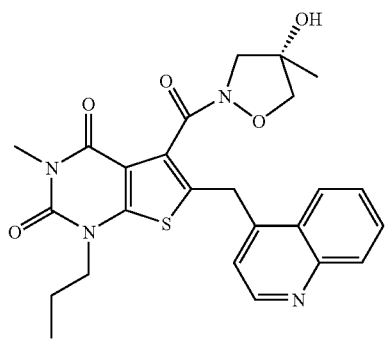

Prepared using the method of example 1 step g) using 1,2,3,4-tetrahydro-3-methyl-2,4-dioxo-1-propyl-6-(4-quinolinylmethyl)-thieno[2,3-d]pyrimidine-5-carboxylic acid sodium salt and the product of example 1 step d).

$\delta^1H_{DMSO}$ 120° C., 0.85 (3H, t), 1.39 (3H, s), 1.66 (2H, sex), 3.23 (3H, s), 3.63-3.87 (6H, m), 4.59 (2H, s), 5.03 (1H, s), 7.42 (1H, s), 7.61 (1H, t), 7.74 (1H, t), 8.04 (1H, d), 8.23 (1H, d), 8.83 (1H, s).

EXAMPLE 8

(4s)-2-[[6-[(2,4-Dichloro-5-thiazolyl)methyl]-1,2,3,4-tetrahydro-3-methyl-1-(2-methylpropyl)-2,4-dioxo-thieno[2,3-d]pyrimidin-5-yl]carbonyl]-4-methyl-4-isoxazolidinol

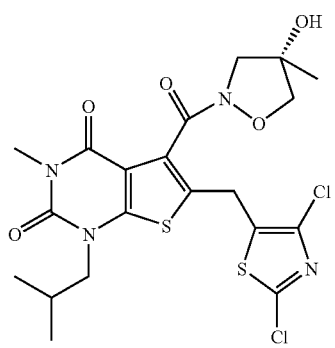

a) 6-[(2,4-Dichloro-5-thiazolyl)hydroxymethyl]-1,2,3,4-tetrahydro-3-methyl-1-(2-methylpropyl)-2,4-dioxo-thieno[2,3-d]pyrimidine-5-carboxylic acid, ethyl ester To a solution of ethyl 3-methyl-1-(2-methylpropyl)-2,4-dioxo-1,2,3,4-tetrahydro-thieno[2,3-d]pyrimidine-5-carboxylate (1.5 g), 2,4-dichlorothiazole-5-carboxaldehyde (1.75 g) and DMPU (1.2 ml) in THF (25 ml) at −78° C., was added LDA (10 mmol). Acetic acid (3 ml) was added and the mixture allowed to warm to ambient temperature. The mixture was then partitioned between ethyl acetate and water, the organics were collected, dried over magnesium sulphate and concentrated to dryness. The residue was purified by normal phase chromatography (3:1 i-hexane: ethyl acetate) to give the sub-title compound as a yellow foam (0.45 g).

$^1H_{CDCl3}$ 0.98 (3H, d), 0.99 (3H, d), 1.40 (3H, t), 2.22-2.35 (1H, m), 3.40 (3H, s), 3.76 (1H, d), 3.81 (1H, d), 4.40-4.47 (2H, m), 6.30 (1H, s).

b) 6-[(2,4-Dichloro-5-thiazolyl)methyl]-1,2,3,4-tetrahydro-3-methyl-1-(2-methylpropyl)-2,4-dioxo-thieno[2,3-d]pyrimidine-5-carboxylic acid, ethyl ester A solution of the product from step a) (0.45 g) in dichloromethane (2 ml) was treated with trifluoroacetic acid (2 ml) and triethylsilane (1.5 ml). The solution was then heated at reflux for 3 hours. The mixture was concentrated to dryness and the residue purified by chromatography on $SiO_2$ (4:1 i-hexane:ethyl acetate) to give the sub-title compound as a yellow oil (294 mg).

$^1H_{CDCl3}$ 0.98 (6H, d), 1.42 (3H, t), 2.27 (1H, non), 3.39 (3H, s), 3.75 (2H, d), 4.24 (2H, s), 4.46 (2H, q).

c) 6-[(2,4-Dichloro-5-thiazolyl)methyl]-1,2,3,4-tetrahydro-3-methyl-1-(2-methylpropyl)-2,4-dioxo-thieno-[2,3-d]pyrimidine-5-carboxylic acid sodium salt Prepared by the method of example 1 step f) using the product of step b).

$^1H_{DMSO}$ 0.92 (6H, d), 2.18 (1H, non), 3.27 (3H, s), 3.75 (2H, d), 4.50 (2H, s).

d) (4S)-2-[[6-[(2,4-Dichloro-5-thiazolyl)methyl]-1,2,3,4-tetrahydro-3-methyl-1-(2-methylpropyl)-2,4-dioxo-thieno[2,3-d]pyrimidin-5-yl]carbonyl]-4-methyl-4-isoxazolidinol Prepared using the method of example 1 step g) using the product of step c) and the product of example 1 step d).

$^1H_{DMSO}$ 120° C., 0.93 (6H, d), 1.40 (3H, s), 2.22 (1H, non), 3.23 (3H, s), 3.65-3.81 (6H, m), 4.25 (2H, s), 5.02 (1H, s).

EXAMPLE 9

(4s)-2-[[6-[(3-Bromo-2-thienyl)methyl]-1,2,3,4-tetrahydro-3-methyl-1-(2-methylpropyl)-2,4-dioxo-thieno[2,3-d]pyrimidin-5-yl]carbonyl]-4-methyl-4-isoxazolidinol

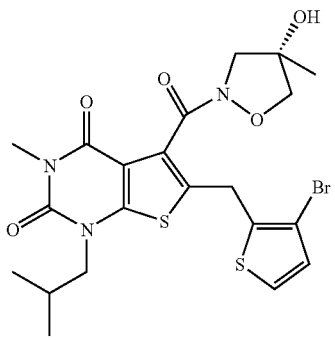

a) 6-[(3-Bromo-2-thienyl)hydroxymethyl]-1,2,3,4-tetrahydro-3-methyl-1-(2-methylpropyl)-2,4-dioxo-thieno[2,3-d]pyrimidine-5-carboxylic acid ethyl ester Prepared according to the method of example 8 step a) using 3-bromo-2-thiophenecarboxaldehyde.

$^1H_{CDCl3}$ 0.96 (3H, d), 0.97 (3H, d), 1.38 (3H, t), 2.27 (1H, non), 3.39 (3H, s), 3.66 (1H, d), 3.71 (1H, dd), 3.79 (1H, dd), 4.38-4.46 (2H, m), 6.38 (1H, d), 6.98 (1H, d), 7.35 (1H, d).

b) 6-[(3-Bromo-2-thienyl)methyl]-1,2,3,4-tetrahydro-3-methyl-1-(2-methylpropyl)-2,4-dioxo-thieno[2,3-d]pyrimidine-5-carboxylic acid ethyl ester Prepared according to the method of example 8 step b) using the product of step a).

$^1H_{CDCl3}$ 0.96 (6H, d), 1.42 (3H, t), 2.25 (1H, non), 3.39 (3H, s), 3.72 (2H, d), 4.32 (2H, s), 4.47 (2H, q), 6.96 (1H, d), 7.23 (1H, d).

c) 6-[(3-Bromo-2-thienyl)methyl]-1,2,3,4-tetrahydro-3-methyl-1-(2-methylpropyl)-2,4-dioxo-thieno[2,3-]pyrimidine-5-carboxylic acid sodium salt Prepared by the method of example 1 step f) using the product of step b).

$^1H_{DMSO}$ 0.87 (6H, d), 2.16 (1H, non), 3.21 (3H, s), 3.66 (2H, d), 4.20 (2H, s), 7.04 (1H, d), 7.53 (1H, d).

d) (4S)-2-[[6-[(3-Bromo-2-thienyl))methyl]-1,2,3,4-tetrahydro-3-methyl-1-(2-methylpropyl)-2,4-dioxothieno[2,3-d]pyrimidin-5-yl]carbonyl]-4-methyl-4-isoxazolidinol Prepared using the method of example 1 step g) using the product of step c) and the product of example 1 step d).

$^1H_{DMSO}$ 120° C., 0.91 (6H, d), 1.40 (3H, s), 2.19 (1H, non), 3.23 (3H, s), 3.65-3.81 (6H, m), 4.24 (2H, s), 5.00 (1H, s), 7.01 (1H,d), 7.51 (1H, d).

EXAMPLE 10

5-[[[(4S)-4-Hydroxy-4-methyl-2-isoxazolidinyl]carbonyl]-3-methyl-1-(1-methylethyl)-6-[[5-methyl-3-(trifluoromethyl)-1H-pyrazol-4-yl]methyl]-thieno[2,3-d]pyrimidine-2,4(1H,3H)-dione

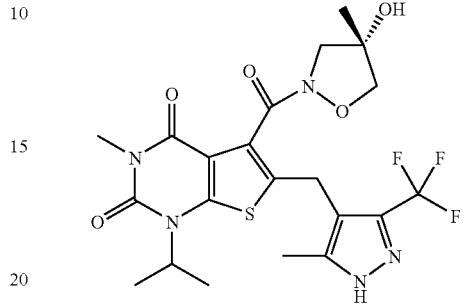

a) 1,2,3,4-Tetrahydro-3-methyl-1-(1-methylethyl)-6-[[5-methyl-3-(trifluoromethyl)-1H-pyrazol-4-yl]methyl]-2,4-dioxo-thieno[2,3-d]pyrimidine-5-carboxylic acid To a suspension of 6-(bromomethyl)-1,2,3,4-tetrahydro-3-methyl-1-(1-methylethyl)-2,4-dioxo-thieno[2,3-d]pyrimidine-5carboxylic acid methyl ester (1.4 g) in chloroform (15 ml) was added zinc acetate (0.82 g) and 1,1,1-trifluoro-2,4-pentanedione (0.55 ml). The mixture was refluxed for 3 hr. then allowed to cool, diluted with dichloromethane and washed with sodium bicarbonate solution. The organic layer was separated and the aqueous was extracted with dichloromethane. The combined organic extracts were dried over magnesium sulfate and evaporated under reduced pressure. The resulting oil was dissolved in ethanol (15 ml) and treated with hydrazine monohydrate (0.24 ml) and the reaction was stirred at ambient temperature for 20 hr. The reaction was evaporated under reduced pressure, dissolved in acetonitrile (10 ml), treated with 2M HCl solution (10 ml) and refluxed for 20 hr. The resulting solid was collected by filtration, washing with water and then diethyl ether to give the sub-title compound as a solid (0.68 g).

MS (ESI) 431 [M+H]$^+$ $^1H_{DMSO}$ 1.44 (6H, d), 2.22 (3H, s), 3.23 (3H, s), 4.20 (2H, s), 4.36 (1H, bs), 13.44 (1H, bs)

b) 5-[[[(4S)-4-Hydroxy-4-methyl-2-isoxazolidinyl]carbonyl]-3-methyl-1-(1-methylethyl)-6-[[5-methyl-3-(trifluoromethyl)-1H-pyrazol-4-yl]methyl]-thieno[2,3-d]pyrimidine-2,4(1H,3H)-dione To a suspension of the product of part a) (0.2 g) in anhydrous dimethylformamide (3 ml), was added triethylamine (0.29 ml), 1-hydroxybenzotriazole (0.078 g) followed by diethyl chlorophosphate (0.075 ml) and the mixture stirred at ambient temperature under nitrogen for 1 hr. 15 min. (4S)-4-Methyl-4-isoxazolidinol hydrochloride (0.07 g) was added and the reaction mixture was stirred at ambient temperature for 20 hr. It was concentrated under reduced pressure, diluted with saturated sodium bicarbonate solution and extracted with dichloromethane. The organic extracts were dried over anhydrous magnesium sulfate, filtered and evaporated under reduced pressure. The residue was purified by column chromatography over silica, eluting with dichloromethane/methanol (98:2) followed by dichloromethane/methanol (96:4) to give the title compound as a solid (0.11 g).

MS (ESI) 516 [M+H]$^+$ $^1$H$_{DMSO}$ 1.24-1.38 (3H, m), 1.44 (6H, s), 2.20 (3H, s), 3.18 (3H, s), 3.62 (2H, m), 3.75 (2H, m), 3.82 (2H, m), 4.37 (1H, bs), 5.23-5.42 (1H, m), 13.38 (1H, bs)

EXAMPLE 11

6-[[3,5-Dimethyl-1-(2-pyridinyl)-1H-pyrazol-4-yl]methyl]-5-[[(4S)-4-hydroxy-4-methyl-2-isoxazolidinyl]carbonyl]-3-methyl-1-(1-methylethyl)thieno[2,3-d]pyrimidine-2,4-(1H,3H)-dione

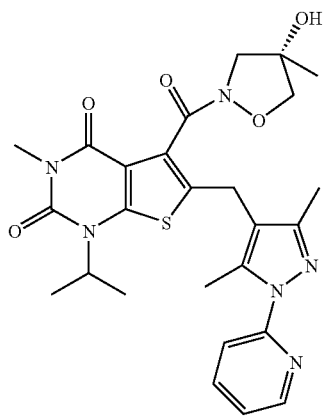

a) 6-[[3,5-Dimethyl-1-(2-pyridyl)-1H-pyrazol-4-yl]methyl-1,2,3,4-tetrahydro-3-methyl-1-(1-methylethyl)-2,4-dioxothieno[2,3-d]pyrimidine-5-carboxylic acid methyl ester Prepared from 6-(bromomethyl)-1,2,3,4-tetrahydro-3-methyl-1-(1-methylethyl)-2,4-dioxothieno[2,3-d]pyrimidine-5-carboxylic acid methyl ester, zinc acetylacetonate hydrate and 2-hydrazinopyridine by the method of example 1 part e) to give the sub-title compound.

MS (ESI) 468 [M+H]$^+$ $^1$H$_{DMSO}$ 1.45 (6H, d), 2.16 (3H, s), 2.56 (3H, s), 3.18 (3H, s), 3.78 (3H, s), 3.95 (2H, s), 4.40 (1H, s, br), 7.31-7.34 (1H, m), 7.79-7.82 (1H, m), 7.93-7.97 (1H, m), 8.45-8.47 (1H, m)

b) 6-[[3,5-Dimethyl-1-(2-pyridyl)-1H-pyrazol-4-yl]methyl-1,2,3,4-tetrahydro-3-methyl-1-(1-methylethyl)-2,4-dioxothieno[2,3-d]pyrimidine-5-carboxylic acid Prepared from the product of part a) by the method of example 6 part b) to give the sub-title compound as a solid
MS (ESI) 454 [M+H]$^+$ c) 6-[[3,5-Dimethyl-1-(2-pyridinyl)-1H-pyrazol-4-yl]methyl]-5-[[(4S)-4-hydroxy-4-methyl-2-isoxazolidinyl]carbonyl]-3-methyl-1-(1-methylethyl)thieno[2,3-d]pyrimidine-2,4-(1H,3H)-dione Prepared from the product of part b) by the method of example 1 part g) to give the title compound as a solid.

MS (APCI) 539 [M+H]$^+$ $^1$H$_{DMSO}$ 1.23-1.46 (9H, m), 2.17-2.18 (3H, m), 2.55-2.58 (3H, m), 3.18-3.19 (3H, m), 3.57-3.94 (6H, m), 4.38 (1H, s, br), 5.42 (1H, d), 7.30-7.34 (1H, m), 7.81 (1H, d), 7.93-7.97 (1H, m), 8.45-8.47 (1H, m)

EXAMPLE 12

5-[[(4S)-4-Hydroxy-4-methyl-isoxazolidinyl]carbonyl]-3-methyl-1-(1-methylethyl)-6-(1H-pyrrolo[2,3-b]pyridin-3-ylmethyl)-thieno[2,3-d]pyrimidine-2,4(1H,3H)-dione

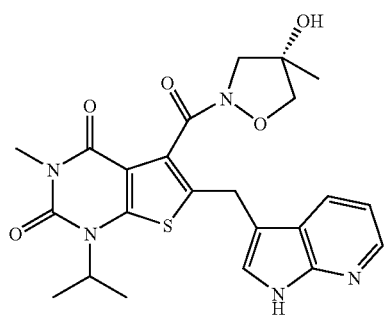

a) 1,2,3,4-Tetrahydro-3-methyl-1-(1-methylethyl)-2,4-dioxo-6-(1H-pyrrolo[2,3-b]pyridin-3-ylmethyl)-thieno[2,3-d]pyrimidine-5-carboxylic acid, sodium salt Prepared from 6-(bromomethyl)-1,2,3,4-tetrahydro-3-methyl-1-(1-methylethyl)-2,4-dioxo-thieno[2,3-d]pyrimidine-5-carboxylic acid, methyl ester (0.45 g, 1.20 mmol) and 7-azaindole (0.17 g, 1.44 mmo) using the method of example 6 part a). The residue was purified by silica chromatography eluting with a gradient from 50% ethyl acetate in isohexane to 100% ethyl acetate to give a colourless oil (0.27 g). 0.1 g of this oil was dissolved in THF (2 mL) and treated with 1M sodium hydroxide solution (0.8 mL) and 0.5 mL of methanol. After 5 hours, a precipitate appeared which was filtered off, washed with THF then with ether to give the sub-title compound as a pale yellow solid.

MS (ES) 399 [M+H]$^+$ b) 5-[[(4S)-4-Hydroxy-4-methylisoxazolidinyl]carbonyl]-3-methyl-1-(1-methylethyl)-6-(1H-pyrrolo[2,3-b]pyridin-3-ylmethyl)-thieno[2,3-d]pyrimidine-2,4(1H,3H)-dione Prepared from the product of example 12 part a) (0.2 g) and the product of example 1 part d) (0.08 g) using the method of example 1 part g). The residue was purified by reverse phase HPLC (95% to 50% aqueous 0.1% ammonium acetate in acetonitrile) to give the title compound as a white foam (0.1 g).

MS (APCI) 484.1642 [M+H]$^+$ $^1$H$_{DMSO}$ 1.23-1.44 (9H, d+s), 3.18 (3H, s), 3.4-4.4 (7H, range of ppm), 5.45 (1H, bs), 7-7.06 (1H, m), 7.43 (1H, s), 7.93-7.99 (1H, m), 8.18-8.20 (1H, d), 11.53 (1H, s).

EXAMPLE 13

(4S)-2-[[6-[[3,5-Dimethyl-1-(4-pyridinyl)-1H-pyrazol-4-yl]methyl]-1,2,3,4-tetrahydro-3-methyl-1-(1-methylethyl)-2,4-dioxo-thieno[2,3-d]pyrimidin-5-yl]carbonyl]-4-methyl-4-isoxazolidinol

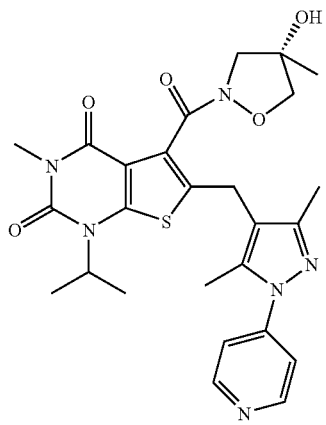

a) 6-[[3,5-Dimethyl-1-(4-pyridinyl)-1H-pyrazol-4-yl]methyl]1,2,3,4-tetrahydro-3-methyl-1-(1-methylethyl)-2,4-dioxo-thieno[2,3-d]pyrimidine-5-carboxylic acid ethyl ester To a solution of the product of example 2 step a) (500 mg) in acetonitrile (5 ml) was added 4-chloropyridine hydrochloride (550 mg). The mixture was then microwave irradiated at 100 W and 140° C. for 20 minutes. The mixture was concentrated to dryness and purified by chromatography on $SiO_2$ (EtOAc to 20% MeOH in EtOAc) to give the sub-title compound as a white solid (200 mg).

$^1H_{CDCl3}$ 1.55 (6H, d), 2.27 (3H, s), 2.41 (3H, s), 3.37 (3H, s), 3.94 (3H, s), 3.96 (2H, s), 4.46 (1H, s), 7.49 (2H, dd), 8.69 (2H, dd).

b) 6-[[3,5-Dimethyl-1-(4-pyridinyl)-1H-pyrazol-4-yl]methyl]-1,2,3,4-tetrahydro-3-methyl-1-(1-methylethyl)-2,4-dioxo-thieno[2,3-d]pyrimidine-5-carboxylic acid sodium salt Prepared by the method of example 1 step f) using the product of step a).

$^1H_{DMSO}$ 1.45 (6H, d), 2.21 (3H, s), 2.46 (3H, s), 3.17 (3H, s), 3.85 (2H, s), 4.32 (1H, s), 7.62 (2H, dd), 8.63 (2H, dd).

c) (4S)-2-[[6-[[3,5-Dimethyl-1-(4-pyridinyl)-1H-pyrazol-4-yl]methyl]-1,2,3,4-tetrahydro-3-methyl-1-(1-methylethyl)-2,4-dioxo-thieno[2,3-d]pyrimidin-5-yl]carbonyl]-4-methyl-4-isoxazolidinol Prepared using the method of example 1 step g) using the product of step b) and the product of example 1 step d).

$^1H_{DMSO}$ 120° C., 1.40 (3H, s), 1.48 (6H, d), 2.18 (3H, s), 2.39 (3H, s), 3.21 (3H, s), 3.65 (1H, S), 3.70 (2H, d), 3.80 (1H, d), 3.89 (2H, s), 4.47 (1H, sep), 7.55 (2H, d), 8.62 (2H, d).

EXAMPLE 14

(4S)-2-[[6-[[3,5-Dimethyl-1-(2-pyrimidinyl)-1H-pyrazol-4-yl]methyl]-1,2,3,4-tetrahydro-3-methyl-1-(1-methylethyl)-2,4-dioxo-thieno[2,3-d]pyrimidin-5-yl]carbonyl]-4-methyl-4-isoxazolidinol

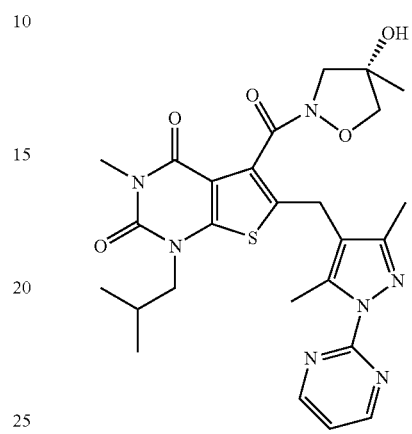

a) 6-[[3,5-Dimethyl-1-(2-pyrimidinyl)-1H-pyrazol-4-yl]methyl]-1,2,3,4-tetrahydro-3-methyl-1-(1-methylethyl)-2,4-dioxo-thieno[2,3-d]pyrimidine-5-carboxylic acid ethyl ester Prepared according to the method of example 13 step a) using 2-chloropyrimidine.

$^1H_{CDCl3}$ 1.52 (6H, d), 2.31 (3H, s), 2.65 (3H, s), 3.37 (3H, s), 3.98 (5H, s), 4.45 (1H, s), 7.19 (1H, t), 8.78 (2H, d).

b) 6-[[3,5-Dimethyl-1-(4-pyrimidinyl)-1H-pyrazol-4-yl]methyl]-1,2,3,4-tetrahydro-3-methyl-1-(1-methylethyl)-2,4-dioxo-thieno[2,3-d]pyrimidine-5-carboxylic acid sodium salt Prepared by the method of example 1 step f) using the product of step a).

$^1H_{D2O}$ 1.49 (6H, s), 2.27 (3H, s), 2.54 (3H, s), 3.31 (3H, s), 3.98 (1H, s), 4.45 (1H, s), 7.51 (1H, s), 8.86 (2H, s).

c) (4S)-2-[[6-[[3,5-Dimethyl-1-(4-pyrimidinyl)-1H-pyrazol-4-yl]methyl]-1,2,3,4-tetrahydro-3-methyl-1-(1-methylethyl)-2,4-dioxo-thieno[2,3-d]pyrimidin-5-yl]carbonyl]-4-methyl-4-isoxazolidinol Prepared by the method of example 1 step f) using the product of step b).

$^1H_{DMSO}$ 120° C. 1.40 (3H, s), 1.47 (6H, d), 2.18 (3H, s), 2.52 (3H, s), 3.21 (3H, s), 3.63-3.72 (3H, m), 3.78-3.83 (1H, m), 4.46 (1H, sep), 4.98 (1H, s), 7.38 (1H, t), 8.81 (2H, d).

EXAMPLE 15

5[[(4S)-4-Hydroxy-4-methyl-2-isoxazolidinyl]carbonyl]-3-methyl-1-(1-methylethyl)-6-[(1-phenyl-1H-pyrazol-4-yl)methyl]-thieno[2,3-d]pyrimidine-2,4-(1H,3H)-dione

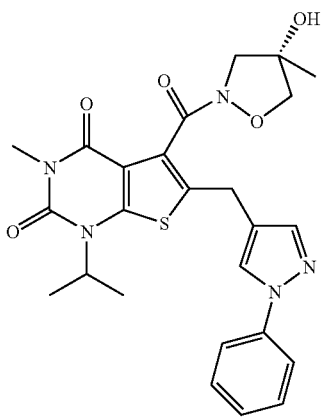

a) 1,2,3,4-Tetrahydro-6-[hydroxy(1-phenyl-1H-pyrazol-4-yl)methyl]-3-methyl-1-(1-methylethyl)-2,4-dioxo-thieno[2,3-d]pyrimidine-5-carboxylic acid ethyl ester To a solution of 1,2,3,4-tetrahydro-3-methyl-1-(1-methylethyl)-2,4-dioxothieno[2,3-d]pyrimidine-5-carboxylic acid ethyl ester (2.0 g), 1-phenyl-1H-pyrazole-4-carboxaldehyde (1.39 g) and 1,3-dimethyl-3,4,5,6-tetrahydro-2(1H)-pyrimidinone (1.63 ml) in anhydrous THF (35 ml) was added a 2.0M solution of LDA (3.72 ml) at −78° C. under nitrogen and the resulting mixture stirred for 3 hr. Glacial acetic acid (1.5 ml) was added, the mixture allowed to warm to room temperature, diluted with water and extracted with ethyl acetate, the organic extracts washed with water, dried over anhydrous magnesium sulfate, filtered and evaporated under reduced pressure. The residue was purified by column chromatography over silica, eluting with i-hexane/ethyl acetate (4:1) followed by i-hexane/ethyl acetate (1:1) to give the sub-title compound (2.32 g).

MS (ESI) 469 [M+H]$^+$ b) 1,2,3,4-Tetrahydro-3-methyl-1-(1-methylethyl)-2,4-dioxo-6-[(1-phenyl-1H-pyrazol-4-yl)methyl]-thieno[2,3-d]pyrimidine-5-carboxylic acid ethyl ester A solution of the product of part a) (2.32 g), trifluoroacetic acid (10 ml) and triethylsilane (5 ml) in dichloromethane (5 ml) was heated at 40° C. under nitrogen for 24 hr. The solvent was removed in vacuo, the residue diluted with aqueous sodium bicarbonate solution and extracted with dichloromethane, the organic extracts washed with water, dried over anhydrous magnesium sulfate, filtered and evaporated under reduced pressure. The residue was purified by column chromatography over silica, eluting with i-hexane/ethyl acetate (9:1) followed by i-hexane/ethyl acetate (4:1) to give the sub-title compound (2.11 g).

MS (ESI) 453 [M+H]$^+$ $^1$H$_{DMSO}$ 1.26 (3H, t), 1.47 (6H, d), 3.19 (3H, s), 4.04 (2H, s), 4.29 (2H, q), 4.37 (1H, s, br), 7.28-7.32 (1H, m), 7.47-7.51 (2H, m), 7.65 (1H, s), 7.78-7.81 (2H, m), 8.40 (1H, s)

c) 1,2,3,4-Tetrahydro-3-methyl-1-(1-methylethyl)-2,4-dioxo-6-[(1-phenyl-1H-pyrazol-4-yl)methyl]-thieno[2,3-d]pyrimidine-5-carboxylic acid Prepared from the product of part b) by the method of example 6 part b) to give the sub-title compound as a solid.

MS (ESI) 425 [M+H]$^+$ d) 5-[[(4S)-4-Hydroxy-4-methyl-2-isoxazolidinyl]carbonyl]-3-methyl-1-(1-methylethyl)-6-[(1-phenyl-1H-pyrazol-4-yl)methyl]thieno[2,3-d]pyrimidine-2,4-(1H,3H)-dione To a solution of the product of part c) (0.5 g), the product of example 1 part d) (0.18 g), and 1-hydroxybenzotriazole (0.36 g) in dichloromethane (10 ml) was added triethylamine (0.36 ml) and N-(3-dimethylaminopropyl)-N'-ethylcarbodiimide hydrochloride (0.45 g) and the mixture stirred at ambient temperature under nitrogen for 18 hr. It was diluted with water and extracted with dichloromethane, the organic extracts were washed successively with 1.0N sodium hydroxide and water, dried over anhydrous magnesium sulfate, filtered and evaporated under reduced pressure. The residue was purified by column chromatography over silica, eluting with ethyl acetate/methanol (99:1) followed by ethyl acetate/methanol (49:1) to give the title compound as a solid (0.14 g).

MS (APCI) 496 [M+H]$^+$ $^1$H$_{DMSO}$ 1.46-1.52 (6H, m), 3.18-3.20 (3H, m), 3.51-4.12 (6H, m), 4.41-4.54 (1H, m), 4.62-4.79 (1H, m), 5.48-5.56 (1H, m), 7.30 (1H, t), 7.49 (2H, t), 7.64-7.68 (1H, m), 7.79 (2H, d), 8.39 (1H, s)

EXAMPLE 16

6-[(8-Fluoroquinolin-4-yl)methyl]-5-{[(4S)-4-hydroxy-4-methylisoxazolidin-2-yl]carbonyl}-1-isopropyl-3-methylthieno[2,3-d]pyrimidine-2,4(1H,3H)-dione

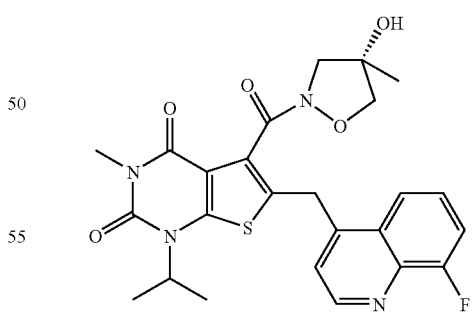

a) 8-Fluoro-4-methyl quinoline

To a solution of 2-fluoroaniline (25 ml) in ethanol (185 ml) was added concentrated hydrochloric acid (21 ml), iron (III) chloride hexahydrate (111 g) and zinc (II) chloride (4.1 g) and the resulting mixture was heated to 60° C. Methyl vinyl ketone (25 ml) was added dropwise over 45 min. then the mixture was refluxed for 2 hrs. The reaction mixture was allowed to cool then evaporated under reduced pressure. The resulting oil was basified to pH 12 with 2M sodium hydroxide solution, filtered through arbocel and then the aqueous was extracted with ethyl acetate (×2). The combined organic extracts were dried over anhydrous magnesium sulfate, filtered and evaporated under reduced pressure. The residue was purified by column chromatography over silica, eluting with i-hexane/diethyl ether (3:1) followed by i-hexane/diethyl ether (2:1) to give the sub-title compound as a solid (8.25 g).

MS (ESI) 162 [M+H]$^+$ $^1$H$_{CDCl3}$ 2.72 (3H, s), 7.28 (1H, m), 7.39 (1H, m), 7.49 (1H, m), 7.77 (1H, d), 8.83 (1H, d)

b) 8-Fluoro-4-quinolinecarboxaldehyde

To a solution of the product of part a) (825 g) in dioxane (20 ml) at 70° C. was added, dropwise over 20 min., a solution of selenium dioxide in dioxane (15 ml) and water (5 ml). The reaction mixture was refluxed for 2.5 hrs. and then ambient temperature for 20 hrs. To the resulting mixture was added ethyl acetate and the suspension was decanted from the solid selenium metal. The organic layer was then evaporated under reduced pressure and the residue was purified by column chromatography over silica, eluting with DCM/diethyl ether (1:1) to give the sub-title compound as a solid (3.61 g).

MS (ESI) 176 [M+H]$^+$ $^1$H$_{CDCl3}$ 7.54 (1H, m), 7.67 (1H, m), 7.38 (1H, d), 8.82 (1H, d), 9.26 (1H, d), 10.52 (1H, s)

c) 6-[(8-Fluoro-4-quinolinyl)hydroxymethyl]-1,2,3,4-tetrahydro-3-methyl-1-(1-methylethyl)-2,4-dioxo-thieno[2,3-d]pyrimidine-5-carboxylic acid, ethyl ester To a solution of 1,2,3,4-tetrahydro-3-methyl-1-(1-methylethyl)-2,4-dioxothieno[2,3-d]pyrimidine-5carboxylic acid, ethyl ester (1.5 g), the product of part b) (1.2 g) and 1,3-dimethyl-3,4,5,6-tetrahydro-2(1H)-pyrimidinone (1.3 ml) in anhydrous THF (20 ml) was added a freshly prepared solution of LDA (2.4 ml of 2.5M n-BuLi, 0.92 ml of diisopropylamine in anhydrous THF (10 ml)) at −78° C. under nitrogen and the resulting mixture stirred for 1.5 hr. Glacial acetic acid (3 ml) was added, the mixture allowed to warm to room temperature, diluted with saturated sodium bicarbonate solution and extracted with DCM (×2), the organic extracts were dried over anhydrous magnesium sulfate, filtered and evaporated under reduced pressure. The residue was purified by column chromatography over silica, eluting with i-hexane/ethyl acetate (80:20) followed by i-hexane/ethyl acetate (60:40) and then by i-hexane/ethyl acetate (25:75) to give the sub-title compound as a solid (0.81 g).

MS (ESI) 472 [M+H]$^+$ $^1$H$_{CDCl3}$ 1.40 (3H, t), 1.46 (6H, d), 3.35 (3H, s), 3.76 (1H, d), 4.36 (1H, bs), 4.48 (2H, quartet), 6.74 (1H, d), 7.44 (2H, m), 7.72 (1H, d), 7.93 (1H, d), 9.06 (1H, d)

d) 6-[(8-Fluoro-4-quinolinyl)methyl]-1,2,3,4-tetrahydro-3-methyl-1-(1-methylethyl-2,4-dioxo-thieno[2,3-d]pyrimidine-5-carboxylic acid ethyl ester To a degassed solution of the product of part c) (0.8 g) in anhydrous THF (15 ml) under nitrogen was added triethylamine (0.85 ml) and trifluoroacetic anhydride (0.4 ml). The reaction mixture was stirred at ambient temperature for 2 hrs. 10% Palladium on charcoal (0.1 g) was added to the mixture under nitrogen and then hydrogenated at 4 bar, ambient temperature for 20 hrs. The mixture was filtered through a pad of celite under nitrogen, washing with ethyl acetate and the filtrate was evaporated under reduced pressure. The resulting oily solid was triturated with diethyl ether:ethyl acetate 95:5, filtered under nitrogen, washed with diethyl ether and dried in vacuo to give the sub-title compound as a solid (0.42 g).

MS (ESI) 456 [M+H]$^+$ $^1$H$_{CDCl3}$ 1.37 (3H, t), 1.54 (6H, d), 3.37 (3H, s), 4.42 (2H, quartet), 4.45 (1H, bs), 4.60 (2H, s), 7.38 (1H, d), 7.43 (1H, m), 7.56 (1H, m), 7.92 (1H, d), 8.95 (1H, d)

e) 6-[(8-Fluoro-4-quinolinyl)methyl]-1,2,3,4-tetrahydro-3-methyl-1-(1-methylethyl)-2,4-dioxo-thieno[2,3-d]pyrimidine-5-carboxylic acid, sodium salt To a degassed solution of the product of part d) (0.42 g) in THF (6 ml)/methanol (1 ml) under nitrogen was added 1N sodium hydroxide solution (1.4 ml) and the mixture was stirred at ambient temperature for 72 hrs. The reaction mixture was evaporated under reduced pressure, azeotroped with diethyl ether (×2) and then triturated with diethyl ether, filtered and dried in vacuo to give the sub-title compound as a solid (0.36 g). MS (ESI) 428 [M+H]$^+$ $^1$H$_{DMSO}$ 1.38 (6H, d), 4.25 (1H, bs), 4.56 (2H, s), 7.55 (2H, m), 7.63 (1H, d), 8.47 (1H, m), 8.86 (1H, d)

f) 6-[(8-Fluoroquinolin-4-yl)methyl]-5-{[(4S)-4-hydroxy-4-methylisoxazolidin-2-yl]carbonyl}-1-isopropyl-3-methylthieno[2,3-d]pyrimidine-2,4(1H,3H)-dione To a suspension of the product of part e) (175 mg) in dichloromethane (3 ml) was added 1-hydroxybenzotriazole (66 mg) and the mixture was stirred at ambient temperature under nitrogen for 20 min. N-(3-Dimethylaminopropyl)-N'-ethylcarbodiimide hydrochloride (95 mg) was added and the mixture was stirred for 1 hr. The product of example 1 part d) (70 mg) and triethylamine (0.07 ml) were added and the mixture stirred at ambient temperature under nitrogen for 72 hrs. The mixture was diluted with water and extracted with dichloromethane (×3), the combined organic extracts were dried over anhydrous magnesium sulfate, filtered and evaporated under reduced pressure. The residue was purified by column chromatography over silica, eluting with dichloromethane/methanol (98:2) and was further purified by reverse phase HPLC (95% to 50% aqueous 0.1% ammonium acetate in acetonitrile) to give the title compound as a white solid (45 mg).

MS (ESI) 513 [M+H]$^+$ $^1$H$_{DMSO}$ 1.16-1.35 (3H, m), 1.43 (6H, m), 3.19 (3H, m), 3.57-3.82 (4H, m), 4.37 (1H, bs), 4.60 (2H, m), 5.22-5.48 (1H, m), 7.61 (3H, m), 8.11 (1H, m), 8.91 (1H, d)

EXAMPLE 17

5-{[(4S)-4-Hydroxy-4-methylisoxazolidin-2-yl]carbonyl}-1-isopropyl-3-methyl-6-(4-pyrimidin-2-yl-benzyl)thieno[2,3-d]pyrimidine-2,4(1H,3H)-dione

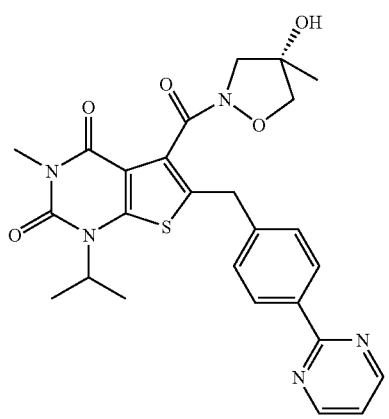

a) 4-(2-Pyrimidinyl)-benzaldehyde

To a degassed suspension of 4-formylphenylboronic acid (100 mg), 2-bromopyrimidine (107 mg) and sodium carbonate (212 mg) in acetonitrile (2 ml)/water (2 ml) was added freshly prepared tetrakis(triphenylphosphine)palladium(0), (40 mg) and the mixture was refluxed under nitrogen, for 20 hrs. The cooled reaction mixture was diluted with water and extracted with ethyl acetate (×2). The combined organic extracts were dried over anhydrous magnesium sulfate, filtered and evaporated under reduced pressure. The residue was purified by column chromatography over silica, eluting with iso-hexane/ethyl acetate (75:25) to afford the sub-title compound as a solid (90 mg).

b) 1,2,3,4-Tetrahydro-6-[hydroxy[4-(2-pyrimidinyl)phenyl]methyl]-3-methyl-1-(1-methylethyl)-2,4-dioxo-thieno[2,3-d]pyrimidine-5-carboxylic acid ethyl ester Prepared from the product of part a) by the method of example 16 part c) to give the sub-title compound as a foam.

MS (ESI) 481 [M+H]$^+$ $^1H_{CDCl_3}$ 1.36 (3H, t), 1.55 (6H, d), 3.36 (3H, s), 3.50 (1H, d), 4.39 (2H, quartet), 4.51 (1H, bs), 6.19 (1H, d), 7.21 (1H, t), 7.60 (2H, d), 8.46 (2H, d), 8.82 (2H, d)

c) 1,2,3,4-tetrahydro-3-methyl-1-(1-methylethyl)-2,4-dioxo-6-[[4-(2-pyrimidinyl)phenyl]methyl]-thieno[2,3-d]pyrimidine-5-carboxylic acid, ethyl ester A solution of the product from step b) (1.37 g) in dichloromethane (10 ml) was treated with trifluoroacetic acid (10 ml) and triethylsilane (10 ml). The solution was then heated at reflux for 48 hours under nitrogen. The mixture was allowed to cool, concentrated to dryness and azeotroped with dichloromethane. The residue was disolved in dichloromethane and washed with saturated sodium carbonate solution (×4) then water (×1), dried over anhydrous magnesium sulfate, filtered and evaporated under reduced pressure. The residue was stirred in iso-hexane for 24 hrs., filtered and washed with iso-hexane to give a solid (800 mg).

To a rapidly stirred solution of the solid (800 mg) in acetone (15 ml) was added, dropwise, a saturated solution of potassium permanagnate in acetone (1 ml) until a dark brown suspension was maintained. The mixture was stirred open to the air at ambient temperature for 15 min. Further saturated potassium permanaganate solution in acetone (0.5 ml) was added and the mixture was stirred for 10 min. (repeated twice more). The resulting mixture was filtered through arbocel and the filtrate was evaporated under reduced pressure. The arbocel was slurried in acetone, filtered and combined with the above residue and evaporated under reduced pressure. The residue was purified by column chromatography over silica, eluting with iso-hexane/ethyl acetate (1:1) to afford the sub-title compound as a solid (400 mg).

MS (ESI) 465 [M+H]$^+$ $^1H_{CDCl_3}$ 1.38 (3H, t), 1.55 (6H, d), 3.37 (3H, s), 4.19 (2H, s), 4.46 (2H, quartet), 4.50 (1H, bs), 7.18 (1H, t), 7.39 (2H, d), 8.42 (2H, d), 8.78 (2H, d)

d) 1,2,3,4-Tetrahydro-3-methyl-1-(1-methylethyl)-2,4-dioxo-6-[[4-(2-pyrimidinyl)phenyl]methyl]-thieno[2,3-d]pyrimidine-5-carboxylic acid monohydrochloride To a suspension of the product of part c) (560 mg) in acetonitrile (5 ml) was added 2M hydrochloric acid solution (5 ml) and the mixture was refluxed for 4 hrs. The mixture was allowed to cool and the solid was collected by filtration, washing with water and dried in a vacuum oven at 50° C. for 20 hrs. to give the sub-title compound as a solid (440 mg).

MS (ESI) 437 [M+H]$^+$ $^1H_{DMSO}$ 1.45 (6H, d), 3.23 (3H, s), 4.35 (2H, s), 4.44 (1H, bs), 7.45 (3H, m), 8.36 (2H, d), 8.90 (2H, d)

e) 5-{[(4S)-4-Hydroxy-4-methylisoxazolidin-2-yl]carbonyl}-1-isopropyl-3-methyl-6-(4-pyrimidin-2-ylbenzyl)thieno[2,3-d]pyrimidine-2,4(1H,3H)-dione Prepared from the product of part d) by the method of example 16 part f) to give the title compound as a solid.

MS (ESI) 522 [M+H]$^+$ $^1H_{DMSO}$ 1.33-1.38 (3H, m), 1.46 (6H, m), 3.19 (3H, s), 3.64-4.15 (6H, m), 4.44 (1H, bs), 5.45 (1H, bs), 7.44 (3H, m), 8.33(2H, d), 8.89 (2H, d)

EXAMPLE 18

5-[[(4S)-4-Hydroxy-4-methyl-2-isoxazolidinyl]carbonyl]-3-methyl-1-(1-methylethyl)-6-[(5-(2-pyridinyl)-2-thienyl)methyl]-thieno[2,3-d]pyrimidine-2,4-(1H,3H)-dione

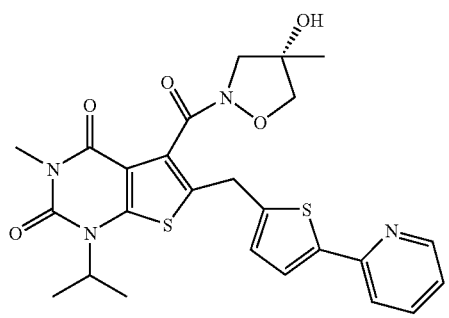

a) 1,2,3,4-Tetrahydro-6-[hydroxy-[(5-(2-pyridinyl)-2-thienyl)methyl]-3-methyl-1-(1-methylethyl)-2,4-dioxo-thieno[2,3-d]pyrimidin-5-carboxylic acid ethyl ester Prepared following the procedure of example 15a) using 5-(2-pyridinyl)-2-thiophenecaboxaldehyde.
MS (ES) 486 [M+H]$^+$ $^1$H$_{DMSO}$ 1.35 (3H, t), 1.58 (6H, d), 3.37 (3H, s), 3.42 (1H, d), 4.40 (2H, q), 4.5 (1H, b), 6.37 (1H, d), 7.07 (1H, d), 7.15 (1H, m), 7.45 (1H, d), 7.63 (1H, d), 7.69 (1H, 8.55 (1H, m)

b) 1,2,3,4-Tetrahydro-3-methyl-1-(1-methylethyl)-2,4-dioxo-6-[(5-(2-pyridinyl)-2-thienyl)methyl]-thieno[2,3-d]pyrimidine-5-carboxylic acid ethyl ester Prepared from the product of part a) following the procedure of example 15 part b)
MS (ESI) 470 [M+H]$^+$ $^1$H$_{DMSO}$ 1.40 (3H, t), 1.55 (6H, d), 3.37 (3H, s), 4.34 (2H, s), 4.4-4.5 (1H, b), 4.45 (2H, s, q), 6.94 (1H, d), 7.14 (1H, m), 7.43 (1H, d), 7.61 (1H, d), 7.67 (1H, td), 8.54 (1H, d)

c) 1,2,3,4-Tetrahydro-3-methyl-1-(1-methylethyl)-2,4-dioxo-6-[(5-(2-pyridinyl)-2-thienyl)methyl]-thieno[2,3-d]pyrimidine-5-carboxylic acid Prepared from the product of part b) by the method of example 6 part b) to give the sub-title compound as a solid.
MS (ESI) 442 [M+H]$^+$ d) 5-[[(4S)-4-Hydroxy-4-methyl-2-isoxazolidinyl]carbonyl]-3-methyl-1-(1-methylethyl)-6-[(5-(2-pyridinyl)-2-thienyl)methyl]thieno[2,3-d]pyrimidine-2,4-(1H,3H)-dione Prepared from the product of part c) by the method of example 15 part d)
MS (APCI) 540 [M+H]$^+$ $^1$H$_{DMSO}$ 1.48 (3H, s), 1.53 (6H, t), 2.32 (3H, s), 2.26 (3H, s), 3.35 (3H, s), 3.43 (1H, d), 3.86 (1H, d), 3.97 (2H, dd), 4.52 (2H, m), 5.41 (1H, s), 7.19 (1H, t), 8.77 (2H, d)

EXAMPLE 19

6-[(1,3-Dimethyl-1H-pyrazolyl)methyl]-5-[[(4S)-4-hydroxy-4-methyl-2-isoxazolidinyl]carbonyl]-3-methyl-1-(1-methylethyl)-thieno[2,3-d]pyrimidine-2,4-(1H,3H)-dione a) 1,2,3,4-Tetrahydro-6-[(1,3-Dimethyl-1H-5-pyrazolyl)methyl]-3-methyl-1-(1-methylethyl)-2,4-dioxo-thieno[2,3-d]pyrimidine-5-carboxylic acid ethyl ester Prepared following the procedure of example 15 a) using 1,3-dimethylpyrazole-5-carboxaldehyde.
MS (ESI) 421 [M+H]$^+$ $^1$H$_{DMSO}$ 1.33 (3H, t), 1.58 (6H, m), 2.24 (3H, s), 3.37 (3H, s), 3.77 (3H, s), 4.35 (2H, m), 4.56 (1H, b), 6.06 (1H, s), 6.13 (1H, d)

b) 1,2,3,4-Tetrahydro-3-methyl-1-(1-methylethyl-2,4-dioxo-6-[(1,3-Dimethyl-1H-5-pyrazol)methyl]-thieno[2,3-d]pyrimidine-5-carboxylic acid ethyl ester Prepared from the product of part a) following the procedure of example 15 part b)
MS (ESI) 405 [M+H]$^+$ $^1$H$_{DMSO}$ 1.39 (3H, t), 1.55 (6H, d), 2.24 (3H, s), 3.37 (3H, s), 3.72 (3H, s), 4.12 (2H, s), 4.43 (2H, q), 4.50 (1H, b), 5.94 (1H, s)

c) 1,2,3,4-Tetrahydro-3-methyl-1-(1-methylethyl)-2,4-dioxo-6-[(1,3-Dimethyl-1H-5-pyrazolyl)methyl]-thieno[2,3-d]pyrimidine-5-carboxylic acid Prepared from the product of part b) by the method of example 6 part b) to give the sub-title compound as a solid.
MS (ESI) 377 [M+H]$^+$ d) 5-[[(4S)-4-Hydroxy-4-methyl-2-isoxazolidinyl]carbonyl]-3-methyl-1-(1-methylethyl)-[(1,3-Dimethyl-1H-5-pyrazolyl)methyl]-thieno[2,3-d]pyrimidine-2,4-(1H,3H)-dione Prepared from the product of part c) by the method of example 15 part d)
MS (APCI) 462 [M+H]$^+$ $^1$H$_{DMSO}$ 1.42 (3H, s), 1.48 (6H, t), 2.08 (3H, s), 3.18 (3H, s), 3.29 (1H, m), 3.63 (3H, s), 3.74 (3H, m), 4.08 (2H, m), 4.44 (1H, bm), 5.42 (1H, s), 5.92 (1H, s)

EXAMPLE 20

6-[(3,5-Dimethyl-4-isothiozolyl)methyl]-5-[[(4S)-4-hydroxy-4-methyl-2-isoxazolidinyl]carbonyl]-3-methyl-1-(1-methylethyl)thieno[2,3-d]pyrimidine-2,4-(1H,3H)-dione

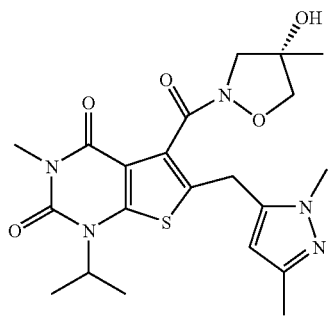

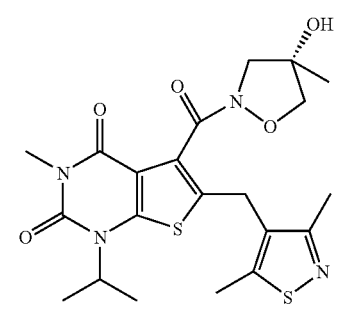

a) 6-[(3,5-Dimethyl-4-isothiazolyl)hydroxymethyl]-1,2,3,4-tetrahydro-3-methyl-1-(1-methylethyl)-2,4-dioxo-thieno[2,3-d]pyrimidine-5-carboxylic acid ethyl ester Prepared by the method of example 15 part a) using 1,2,3,4-tetrahydro-3-methyl-1-(1-methylethyl)-2,4-dioxothieno[2,3-d]pyrimidine-5-carboxylic acid ethyl ester, and 3,5-dimethyl-4-isothiazolecarboxaldehyde.

MS (ESI) 438 [M+H]$^+$ $^1$H$_{DMSO}$ 1.04 (3H, t), 1.51-1.54 (6H, m), 2.25 (3H, s), 2.42 (3H, s), 3.16 (3H, s), 3.68-3.88 (2H, m), 4.61 (1H, s, br), 6.01 (1H, d), 6.75 (1H, d).

b) 6[(3,5-Dimethyl-4-isothiazolyl)methyl]-1,2,3,4-tetrahydro-3-methyl-1-(1-methylethyl)-2,4-dioxo-thieno[2,3-d]pyrimidine-5-carboxylic acid ethyl ester Prepared from the product of part a) by the method of example 15 part b).

MS (ESI) 422 [M+H]$^+$ $^1$H$_{DMSO}$ 1.25 (3H, t), 1.45 (6H, d), 2.29 (3H, s), 2.46 (3H, s), 3.17 (3H, s), 4.07 (2H, s), 4.21 (2H, q), 4.40 (1H, s, br).

c) 6-[(3,5-Dimethyl-4-isothiazolyl)methyl]-1,2,3,4-tetrahydro-3-methyl-1-(1-methylethyl)-2,4-dioxo-thieno[2,3-d]pyrimidine-5-carboxylic acid A solution of the product of step b) (0.26 g) in acetonitrile (10 ml) and 2.5N hydrochloric acid (10 ml) was heated under reflux for 6 h. It was concentrated in vacuo, diluted with water and extracted into dichloromethane, the organic extracts washed with water, dried over anhydrous magnesium sulfate, filtered and evaporated under reduced pressure to afford the subtitle compound.

MS (ESI) 394 [M+H]$^+$ d) 6-[(3,5-Dimethyl-4-isothiozolyl)methyl]-5-[[(4S)-4-hydroxy-4-methyl-2-isoxazolidinyl]carbonyl]-3-methyl-1-(1-methylethyl)thieno[2,3-d]pyrimidine-2,4-(1H,3H)-dione Prepared from the product of part c) by the method of example 10 part b).

MS (APCI) 479 [M+H]$^+$ $^1$H$_{DMSO}$ 1.31-1.46 (9H, m), 2.3-2.32 (3H, m), 2.47-2.48 (3H, m), 3.17-3.18 (3H, m), 3.42-4.02 (6H, m), 4.36 (1H, s, br), 5.41 (1H, d).

EXAMPLE 21

5-[[(4S)-4-Hydroxy-4-methyl-2-isoxazolidinyl]carbonyl]-3-methyl-1-(1-methytlethyl)-6-[[1-(2-thiazolyl)-1H-pyrazol-4-yl]methyl]thieno[2,3-d]pyrimidine-2,4-(1H,3H)-dione

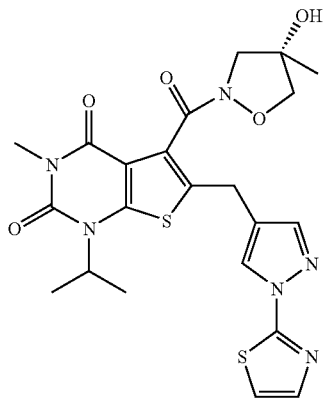

a) 1-(Diphenylmethyl)-1H-pyrazole-4-carboxylic acid ethyl ester

A suspension of 1H-pyrazole-4-carboxylic acid ethyl ester (1.0 g), benzhydryl chloride (1.9 ml) and potassium carbonate (1.48 g) in anhydrous 1-methyl-2-pyrrolidinone (10 ml) was heated at 100° C. under nitrogen for 6 h. It was diluted with water and extracted with ethyl acetate, the organic extracts washed with water, dried over anhydrous magnesium sulfate, filtered and evaporated under reduced pressure. The residue was purified by column chromatography over silica, eluting with i-hexane/ethyl acetate (4:1) followed by i-hexane/ethyl acetate (2:1) to give the sub-title compound (2.18 g).

$^1$H$_{CDCl_3}$ 1.32 (3H, t), 4.27 (2H, q), 6.77 (1H, s), 7.10-7.12 (4H, m), 7.32-7.40 (10H, m), 7.74 (1H, s), 7.99 (1H, s).

b) 1-(Diphenylmethyl)-1H-pyrazole-4-carboxaldehyde

To a solution of the product of part a) (2.18 g) in anhydrous THF (40 ml) was added 1.1M aluminum hydride solution in THF (10 ml) dropwise at 0° C. under nitrogen and the resulting mixture stirred at room temperature for 2 h. It was carefully poured into water, mixed with ethyl acetate and filtered. It was extracted with ethyl acetate, the organic extracts washed with water, dried over anhydrous magnesium sulfate, filtered and evaporated under reduced pressure. The residue was dissolved in acetone (6 ml) and the solution cooled to 10° C. then treated with chromium trioxide solution (0.66 g) in water (4 ml) and sulphuric acid (0.53 ml), stirred at room temperature for 2 h, and extracted with ethyl acetate, the organic extracts washed with water, dried over anhydrous magnesium sulfate, filtered and evaporated under reduced pressure. The residue was purified by column chromatography over silica, eluting with i-hexane/ethyl acetate (9:1) followed by i-hexane/ethyl acetate (3:1) to give the sub-title compound (1.2 g).

$^1$H$_{DMSO}$ 7.05 (1H, s), 7.19-7.22 (4H, m), 7.32-7.42 (6H, m), 8.08 (1H, s), 9.81 (1H, s).

c) 6-[[1-(Diphenylmethyl)-1H-pyrazol-4-yl]hydroxymethyl]-1,2,3,4-tetrahydro-3-methyl-1-(1-methylethyl)-2,4-dioxo-thieno[2,3-d]pyrimidine-5-carboxylic acid ethyl ester Prepared from the product of part b) and 1,2,3,4-tetrahydro-3-methyl-1-(1-methylethyl)-2,4-dioxothieno[2,3-d]pyrimidine-5-carboxylic acid ethyl ester by the method of example 15 part a).

MS (ESI) 559 [M+H]$^+$ d) 1,2,3,4-Tetrahydro-3-methyl-1-(1-methylethyl)-2,4-dioxo-6-(1H-pyrazol-4-ylmethyl)thieno[2,3-d]pyrimidine-5-carboxylic acid, ethyl ester Prepared from the product of part c) by the method of example 15 part b).

MS (ESI) 377 [M+H]$^+$ $^1$H$_{DMSO}$ 1.28 (3H, t), 1.46 (6H, d), 3.19 (3H, s), 3.96 (2H, s), 4.30 (2H, q), 4.48 (1H, s, br), 7.51 (2H, s).

e) 1,2,3,4-Tetrahydro-3-methyl-1-(1-methylethyl)-2,4-dioxo-6-[[1-(2-thiazolyl)-1H-pyrazol-4-ylmethyl]thieno[2,3-d]pyrimidine-5-carboxylic acid To a solution of the product of step d) (500 mg) in acetonitrile (2 ml) was added 2-bromothiazole (0.24 ml). The mixture was then microwave irradiated at 200 W and 140° C. for 20 minutes. It was cooled, diluted with acetonitrile (5 ml), 2.5N HCl (5 ml) added and the mixture heated under reflux for 18 h. It was cooled, the precipitated solid collected by filtration and recrystallised from DMF to give the sub-title compound (0.1 g).

MS (ESI) 432 [M+H]$^+$ f) 5-[[(4S)-4-Hydroxy-4-methyl-2-isoxazolidinyl]carbonyl]-3-methyl-1-(1-methylethyl-6-[[1-(2-thiazolyl)-1H-pyrazol-4-yl]methyl]thieno[2,3-d]pyrimidine-2,4-(1H,3H)-dione Prepared from the product of part e) by the method of example 10 part b).

MS (APCI) 517 [M+H]$^+$ $^1$H$_{DMSO}$ 1.31-1.48 (9H, m), 3.19-3.20 (3H, m), 3.36-4.06 (6H, m), 4.48 (1H, s, br), 5.43-5.46 (1H, m), 7.52 (2H, s), 7.63 (1H, d), 7.74-7.80 (1H, m), 8.37-8.44 (1H, m).

EXAMPLE 22

6-[(4-Fluorophenyl)methyl]-5-[[(4S)-4-hydroxy-4-methyl-2-isoxazolidinyl]carbonyl]-3-methyl-1-(1-methylethyl)thieno[2,3-d]pyrimidine-2,4-(1H,3H)-dione

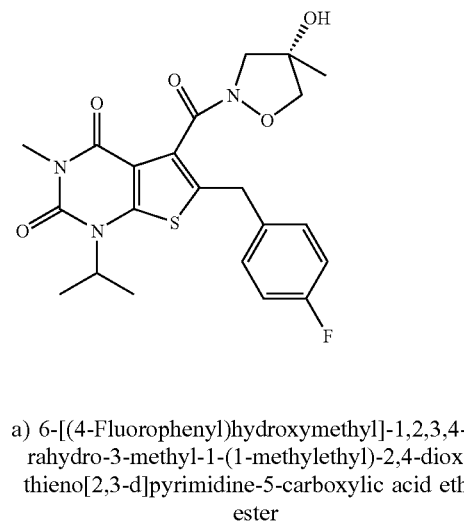

a) 6-[(4-Fluorophenyl)hydroxymethyl]-1,2,3,4-tetrahydro-3-methyl-1-(1-methylethyl)-2,4-dioxo-thieno[2,3-d]pyrimidine-5-carboxylic acid ethyl ester Prepared by the method of example 15 part a) using 1,2,3,4-tetrahydro-3-methyl-1-(1-methylethyl)-2,4-dioxothieno[2,3-d]pyrimidine-5-carboxylic acid ethyl ester and 4-fluorobenzaldehyde.

MS (ESI) 421 [M+H]$^+$ b) 6-[(4-Fluorophenyl)methyl]-1,2,3,4-tetrahydro-3-methyl-1-(1-methylethyl)-2,4-dioxo-thieno[2,3-d]pyrimidine-5-carboxylic acid ethyl ester Prepared from the product of part a) by the method of example 15 part b).

MS (ESI) 405 [M+H]$^+$ $^1$H$_{DMSO}$ 1.18 (3H, t), 1.45 (6H, d), 3.18 (3H, s), 4.10 (2H, s), 428 (2H, q), 4.43 (1H, s, br), 7.15-7.19 (2H, m), 7.29-7.33 (2H, m).

c) 6-[(4-Fluorophenyl)methyl]-1,2,3,4-tetrahydro-3-methyl-1-(1-methylethyl)-2,4-dioxo-thieno[2,3-d]pyrimidine-5-carboxylic acid Prepared from the product of part b) by the method of example 20 part c).

MS (ESI) 377 [M+H]$^+$ d) 6-[(4-Fluorophenyl)methyl]-5-[[(4S)-4-hydroxy-4-methyl-2-isoxazolidinyl]carbonyl]-3-methyl-1-(1-methylethyl)thieno[2,3-d]pyrimidine-2,4-(1H,3H)-dione Prepared from the product of part c) by the method of example 10 part b).

MS (APCI) 462 [M+H]$^+$ $^1$H$_{DMSO}$ 1.23-1.26 (9H, m), 3.19-3.24 (3H, m), 3.56-4.10 (6H, m), 4.45 (1H, S, br), 5.43 (1H, s), 7.15 (2H, t), 7.30-7.37 (2H, m).

EXAMPLE 23

5-[[(4S)-4-Hydroxy-4-methyl-2-isoxazolidinyl]carbonyl]-3-methyl-1-(1-methylethyl)-6-(1H-1,2,3-triazol-1-ylmethyl)thieno[2,3-d]pyrimidine-2,4-(1H,3H)-dione

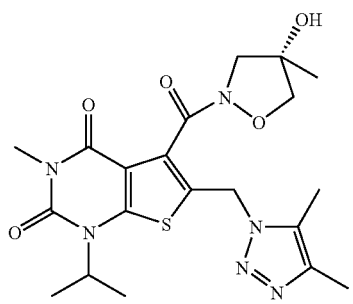

a) 6-(Azidomethyl)-1,2,3,4-tetrahydro-3-methyl-1-(1-methylethyl)-2,4-dioxo-thieno[2,3-d]pyrimidine-5-carboxylic acid methyl ester To a solution of 6-(bromomethyl)-1,2,3,4-tetrahydro-3-methyl-1-(1-methylethyl)-2,4-dioxothieno[2,3-d)]pyrimidine-5-carboxylic acid methyl ester (0.5 g) in acetonitrile (4 ml) was added a solution of sodium azide (0.95 g) in acetonitrile (1 ml) and water (0.5 ml) and the resulting mixture stirred at room temperature under nitrogen for 18 h. It was diluted with water and extracted into ethyl acetate, the organic extracts washed with water, dried over anhydrous magnesium sulfate, filtered and evaporated under reduced pressure to give the sub-title compound as a solid (0.39 g).

MS (ESI) 338 [M+H]+ $^1H_{CDCl3}$ 1.63 (6H, d), 3.38 (3H, s), 3.98 (3H, s), 4.54 (2H, s), 4.68 (1H, s, br).

b) 6-[(4,5-Dimethyl-1H-1,2,3-triazol-1-yl)methyl]-1,2,3,4-tetrahydro-3-methyl-1-(1-methylethyl)-2,4-dioxo-thieno[2,3-d]pyrimidine-5-carboxylic acid, methyl ester A mixture of the product of part a) (0.39 g), phenyl vinyl sulphoxide (1.0 g) and chlorobenzene (10 ml) was heated at 130° C. for 8 h. It was cooled and concentrated in vacuo. The residue was purified by column chromatography over silica, eluting with i-hexane/ethyl acetate (4:1) followed by i-hexane/ethyl acetate (1:1) to give the sub-title compound (0.39 g).

MS (ESI) 364 [M+H]+ $^1H_{DMSO}$ 1.48 (6H, d), 3.18 (3H, s), 3.86 (3H, s), 4.51 (1H, s, br), 5.82 (2H, s), 7.76 (1H, s), 8.13 (1H, s).

c) 6[(4,5-Dimethyl-1H-1,2,3-triazol-1-yl)methyl]-1,2,3,4-tetrahydro-3-methyl-1-(1-methylethyl)-2,4-dioxo-thieno[2,3-d]pyrimidine-5-carboxylic acid Prepared from the product of part b) by the method of example 20 part c).

MS (ESI) 350 [M+H]+ d) 5-[[(4S)-4-hydroxy-4-methyl-2-isoxazolidinyl]carbonyl]-3-methyl-1-(1-methylethyl)-6-(1H-1,2,3-triazol-1-ylmethyl)thieno[2,3-d]pyrimidine-2,4-(1H,3H)-dione Prepared from the product of part c) by the method of example 10 part b).

MS (APCI) 435 [M+H]+ $^1H_{DMSO}$ 1.23-1.49 (9H, m), 3.18-3.19 (3H, m), 3.37-3.99 (4H, m), 4.49 (1H, s, br), 5.43-5.52 (1H, m), 5.70-5.81 (2H, m), 7.76 (1H, s), 8.07-8.18 (1H, m).

EXAMPLE 24

6-[(6-Chloroimidazo[1,2-a]pyridin-3-yl)methyl]-5-[[(4S)-4-hydroxy-4-methyl-2-isoxazolidinyl]carbonyl]-3-methyl-1-(1-methylethyl)thieno[2,3-d]pyrimidine-2,4-(1H,3H)-dione

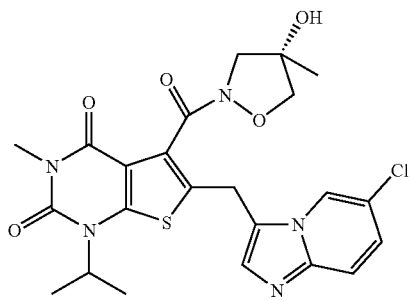

a) 6-[(6-Chloroimidazo[1,2-a]pyridin-3-yl)hydroxymethyl-1,2,3,4-tetrahydro-3-methyl-1-(1-methylethyl)-2,4-dioxo-thieno[2,3-d]pyrimidine-5-carboxylic acid ethyl ester Prepared from 1,2,3,4-tetrahydro-3-methyl-1-(1-methylethyl)-2,4-dioxothieno[2,3-d]pyrimidine-5-carboxylic acid, ethyl ester and 6-chloroimidazo[1,2-a]pyridine-3-carboxaldehyde by the method of example 15 part a).

MS (ESI) 477 and 479 [M+H]+ $^1H_{DMSO}$ 1.02 (3H, t), 1.52 (6H, dd), 3.91-3.99 (2H, m), 4.58 (1H, s, br), 6.49 (1H, d), 7.09 (1H, d), 7.36 (1H, dd), 7.48 (1H, s), 7.67 (1H, d), 8.55 (1H, s).

b) 6-[(6-Chloroimidazo[1,2-a]pyridin-3-yl)methyl]-1,2,3,4-tetrahydro-3-methyl-1-(1-methylethyl)-2,4-dioxo-thieno[2,3-d]pyrimidine-5-carboxylic acid, ethyl ester Prepared from the product of part a) by the method of example 15 part b).

MS (ESI) 461 and 463 [M+H]+ $^1H_{DMSO}$ 1.18 (3H, t), 1.44 (6H, d), 3.18 (3H, s), 4.26 (2H, q), 4.43 (1H, s, br), 4.54 (3H, s), 7.32 (1H, dd), 7.56 (1H, s), 7.65 (1H, d), 8.57 (1H, s).

c) 6-[(6-Chloroimidazo[1,2-a]pyridin-3-yl)methyl]-1,2,3,4-tetrahydro-3-methyl-1-(1-methylethyl)-2,4-dioxo-thieno[2,3-d]pyrimidine-5-carboxylic acid Prepared from the product of part b) by the method of example 20 part c).

MS (ESI) 433 and 435 [M+H]+ d) 6-[(6-Chloroimidazo[1,2-a]pyridin-3-yl)methyl]-5-[[(4S)-4-hydroxy-4-methyl-2-isoxazolidinyl]carbonyl]-3-methyl-1-(1-methylethyl)thieno[2,3-d]pyrimidine-2,4-(1H,3H)-dione Prepared from the product of part c) by the method of example 10 part b).

MS (APCI) 518 and 520 [M+H]$^+$ $^1$H$_{DMSO}$ 1.32-1.44 (9H, m), 3.18-3.19 (3H, m), 3.64-3.83 (4H, m), 4.35-4.53 (3H, m), 5.45-5.46 (1H, m), 7.30 (1H, dd), 7.59-7.65 (2H, m), 8.64-8.71 (1H, m).

EXAMPLE 25

5-[[(4S)-4-hydroxy-4-methylisoxazolidin-2-yl]carbonyl]-3-methyl-1-(1-methylethyl)-6-[[4-(2-pyridinyl)phenyl]methyl]-thieno[2,3-d]pyrimidine-2,4(1H,3H)-dione

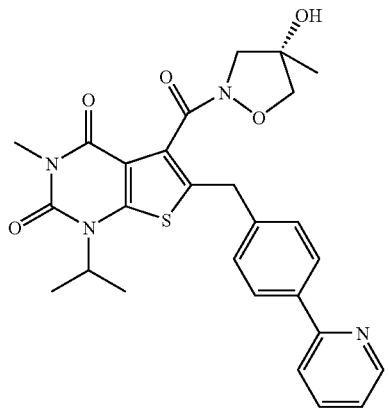

a) 1,2,3,4-Tetrahydro-6-[hydroxy[4-(2-pyridinyl)phenyl]methyl]-3-methyl-1-(1-methylethyl)-2,4-dioxo-thieno[2,3-d]pyrimidine-5-carboxylic acid, ethyl ester Lithium diisopropylamide, freshly made by adding n-buthyllithium (1.1 mL, 2.5M in hexanes) to a solution of diisopropylamine (0.46 mL) in dry tetrahydrofuran under nitrogen at 0° C. and stirring for 20 min, was added to a solution of 1,2,3,4-tetrahydro-3-methyl-1-(1-methylethyl)-2,4-dioxo-thieno[2,3-d]pyrimidine-5-carboxylic acid, ethyl ester (0.7 g), 4-(2-pyridyl)benzaldehyde (0.52 g) and DMPU (057 mL) in dry tetrahydrofuran under nitrogen at −78° C. The reaction mixture was stirred at −78° C. for 4 hours then quenched with glacial acetic acid (10 mL) and allowed to reach room temperature. Water was added and the mixture was extracted with ethyl acetate (twice). The organics were washed with brine, dried over MgSO$_4$ and concentrated under vacuum to give a brown oil which was purified by silica chromatography eluting with isohexane/ethyl acetate (1/1) to give the sub-title compound as a pale yellow foam (0.47 g).

MS (ES) 480 [M+H]$^+$ $^1$H$_{DMSO}$ 1.15-1.23 (3H, t), 1.47-1.53 (6H, d), 3.17 (3H, s), 4.16-4.24 (2H, q), 4.55 (1H, bs), 5.97-5.98 (1H, d), 6.82-6.84 (1H, d), 7.32-7.37 (1H, m), 7.47-7.50 (2H, d), 7.84-7.96 (2H, m), 8.05-8.08 (2H, d), 8.64-8.66 (1H,d).

b) 1,2,3,4-tetrahydro-3-methyl-1-(1-methylethyl)-2,4-dioxo-6-[[4-(2-pyridinyl)phenyl]methyl]-thieno[2,3-d]pyrimidine-5-carboxylic acid, ethyl ester The product of part a) (0.47 g) dissolved in dichloromethane (2 mL) was treated with trifluoroacetic acid (2 mL) and triethylsilane (1 mL) and stirred at ambient temperature for 18 hours. Dichloromethane and trifluoroacetic acid were evaporated. Water was added and the reaction mixture was basified with sodium carbonate then extracted with dichloromethane (twice). The organics were washed with brine, dried over MgSO$_4$ and concentrated under vacuum to give a white solid which was purified by silica chromatography eluting with isohexane/ethylacetate (3/2) to give the sub-title compound as a colourless oil which solidified (0.39 g).

MS (ES) 464 [M+H]$^+$ $^1$H$_{DMSO}$ 1.23-1.28 (3H, t), 1.44-1.46 (6H, d), 3.18 (3H, s), 4.16 (2H, s), 4.27-4.31 (2H, q), 4.33 (1H, bs), 7.32-7.36 (1H, m), 7.36-7.38 (2H, d), 7.85-7.89 (1H, t), 7.93-7.95 (1H, d), 8.04-8.06 (2H, d), 8.64-8.66 (1H, d).

c) 1,2,3,4-tetrahydro-3-methyl-1-(1-methylethyl)-2,4-dioxo-6-[[4-(2-pyridinyl)phenyl]methyl]-thieno[2,3-d]pyrimidine-5-carboxylic acid Prepared from a solution of the product of part b) (0.39 g) in acetonitrile (15 mL) which was treated with 2M hydrochloric acid (4 mL) and heated at reflux for 15 hours. The mixture was concentrated to dryness. The residue was triturated with water, filtered and washed with ether then dried in a vacuum oven at 55° C. to give the sub-title compound as a white solid (0.22 g).

MS (ES) 436 [M+H]$^+$ d) 5-[[(4S)-4-Hydroxy-4-methylisoxazolidin-2-yl]carbonyl]-3-methyl-1-(1-methylethyl)-6-[[4-(2-pyridinyl)phenyl]methyl]-thieno[2,3-d]pyrimidine-2,4(1H,3H)-dione To a solution of the product of part c) (0.22 g) in dichloromethane was added oxalyl chloride (0.132 mL) followed by 2 drops of dimethylformamide under nitrogen. The reaction mixture was stirred at ambient temperature for 1 hour then concentrated to dryness. The residue was dissolved in dichloromethane then added to a solution of (4S)-4-hydroxy-4-methylisoxazolidine hydrochloride (0.14 g) and triethylamine (0.3 mL) in dichloromethane. The reaction mixture was stirred at room temperature for 2 hours. Water was added. The reaction mixture was partitionned and the organics were dried over MgSO$_4$ then concentrated under vacuum. The residue was purified by silica chromatography eluting with 4% methanol in dichloromethane then again with ethyl acetate. Finally, another purification by reverse phase HPLC eluting with acetonitrile/0.2% NH$_3$ in water was carried out to give the title compound as a white solid (0.1 g).

MS (APCI) 521.1860 [M+H]$^+$ δ$^1$H$_{CDCl3}$ 1.52-1.56 (9H, m), 3.35 (3H, s), 3.42-3.46 (1H, d), 3.86-4.01 (2H, ABq), 4.18 (2H, s), 4.52-4.56 (2H, d+bs), 5.42 (1H, s), 7.21-7.24 (1H, m), 7.34-7.42 (2H, d), 7.69-7.78 (2H. m), 7.78-7.94 (2H, d), 8.67-8.69 (1H, d).

EXAMPLE 26

(4S)-4-Methyl-2-[[1,2,3,4-tetrahydro-3-methyl-1-(1-methylethyl)-6-[[5-methyl-1-(2-pyrimidinyl)-3-(trifluoromethyl)-1H-pyrazol-4-yl]methyl]-2,4-dioxothieno[2,3-d]pyrimidin-5-yl]carbonyl]-4-isoxazolidinol

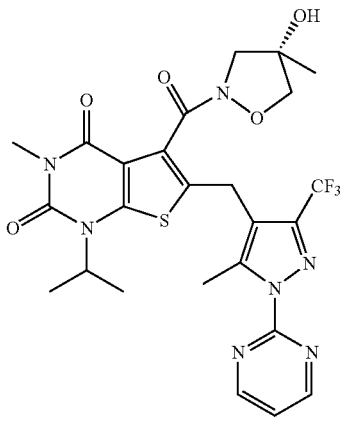

A mixture of the product of example 10 part b) (279 mg), 2-bromopyrimidine (300 mg), copper(I) iodide (95 mg), trans-cyclohexanediamine (55 mg) and potassium carbonate (300 mg) in dioxane (2 ml) was heated at 100° C. for 16 hours under nitrogen. The reaction mixture was concentrated to dryness and purified by silica chromatography eluting with an ethyl acetate to 10% methanol/ethyl acetate gradient, followed by RPHPLC to give the title compound as a white solid (105 mg).

MS (APCI+ve) 494 [M+H]+ $\delta^1 H_{DMSO}$,120° C. 1.40 (3H, s), 1.47 (6H, d), 2.53 (3H, s), 3.21 (3H, s), 3.64-3.72 (3H, m), 3.80 (1H, d), 4.07 (2H, s), 4.46 (sep, 1H), 7.59 (1H, t), 8.94 (2H, d)

EXAMPLE 27

(4S)-2-[[6-[[3,5-Dimethyl-1-(2-pyrimidinyl)-1H-pyrazol-4-yl]methyl]-1,2,3,4-tetrahydro-3-methyl-1-(1-methylethyl)-2,4-dioxothieno[2,3-d]pyrimidin-5-yl]carbonyl]-4-ethyl-4-isoxazolidinol

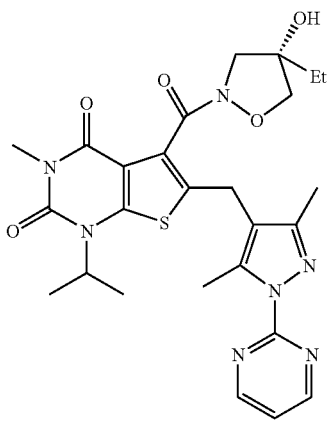

a) (S)-([2-Ethyloxiranyl]methyl) 3-nitro-benzenesulfonate

A mixture of 2-ethylprop-2-en-1-ol (1.5 g), powdered 3A° molecular sieves (620 mg) and (−)-D-diethyltartrate (177 µl) was stirred in dichloromethane (35 ml) under nitrogen for 24 hours. The mixture was cooled to −20° C. and titanium tetraisopropoxide (265 µl) was added. After stirring for 2 hours at −20° C. cumene hydroperoxide (6.4 ml) was added and after a further 2 hours the reaction allowed to warm to −5° C. before being quenched by the slow addition of trimethylphosphite (3.4 ml).

Triethylamine (3.7 ml), DMAP (265 mg) and a solution of 3-nitrobenzenesulphonyl chloride (3.95 g) in dichloromethane (25 ml) were then added sequentially and the mixture stirred at room temperature for 3 hours. The reaction mixture was poured onto silica and eluted with dichloromethane to give the sub-title compound as a yellow oil (4.8 g).

$\delta^1 H_{CDCl3}$ 0.91 (3H, t), 1.61 (1H, sex), 1.81 (1H, sex), 2.68 (1H, d), 2.70 (1H, d), 4.09 (1H, d), 4.31 (1H, d), 7.81 (1H, t), 8.25 (1H, ddd), 8.53 (1H, ddd), 8.77 (1H, t).

b) 2-[[(2S)-2-Ethyloxiranyl]methoxy]-1H-isoindole-1,3(2H)-dione

The sub-title compound was prepared using the method of example 1 part a) using the product of part a).

$^1H_{CDCl3}$ 1.04 (3H, t), 1.89 (1H, dq), 2.11 (1H, dq), 2.72 (1H, d), 2.75 (1H, d), 4.22 (1H, d), 4.25 (1H, d), 7.72-7.77 (2H, m), 7.82-7.87 (2H, m).

c) 2-[[(2R)-3-Chloro-2-hydroxy-2-ethylpropyl]oxy]-1H-isoindole-1,3(2H)-dione The sub-title compound was prepared using the method of example 1 part b) using the product of part b).

$^1H_{CDCl3}$ 1.01 (3H, t), 1.71 (1H, dq), 1.75 (1H, dq), 3.70 (1H, d), 3.75 (1H, d), 4.08 (1H, d), 4.50 (1H, d), 7.75-7.80 (2H, m), 7.84-7.88 (2H, m).

d) 2-[[(4S)-4-Hydroxy-4-ethyl-2-isoxazolidinyl]carbonyl]-benzoic acid methyl ester The sub-title compound was prepared using the method of example 1 part c) using the product of part c).

$^1H_{CDCl3}$ 1.09 (3H, t), 1.82 (2H, q), 2.01 (1H, s), 3.59 (1H, d), 3.84 (1H, d), 3.92 (3H, s), 3.94 (1H, d), 4.32 (1H, d), 7.45 (1H, d), 7.49 (1H, t), 7.62 (1H, t), 7.99 (1H, d). HPLC: (9010IHIP.M) 4.6×250 mm kromasil DMB column, ee>99% e) (4S)-4-Ethyl-4-isoxazolidinol hydrochloride

The sub-title compound was prepared using the method of example 1 part d) using the product of part d).

$^1H_{DMSO}$ 0.94 (3H, t), 1.66-1.79 (2H, M), 3.28 (1H, d), 3.38 (1H, d), 3.90 (1H, d), 4.05 (1H, d).

f) (4S)-2-[[6-[[3,5-Dimethyl-1-(2-pyrimidinyl)-1H-pyrazol-4-yl]methyl]-1,2,3,4-tetrahydro-3-methyl-1-(1-methylethyl)-2,4-dioxothieno[2,3-d]pyrimidin-5-yl]carbonyl]-4-ethyl-4-isoxazolidinol The title compound was prepared from the product of example 11 part b) using the method of example 15 part d).

MS (APCI+ve) 554 [M+H]+ $\delta^1 H_{DMSO}$,120° C. 0.94 (3H, t), 1.47 (6H, d), 1.71 (2H, q), 2.18 (3H, s), 2.52 (3H, s), 3.20 (3H, s), 3.64 (1H, m), 3.74-3.8 (3H, m), 3.89 (2H, s), 4.46 (sep, 1H), 7.38 (1H, t), 8.81 (2H, d)

EXAMPLE 28

(4S)-2-[[6-[[1-(2,3-dihydro-2-oxo-4-pyrimidinyl)-3,5-dimethyl-1H-pyrazol-4-yl]methyl]-1,2,3,4-tetrahydro-3-methyl-1-(1-methylethyl)-2,4-dioxothieno[2,3-d]pyrimidin-5-yl]carbonyl]-4-methyl-4-isoxazolidinol

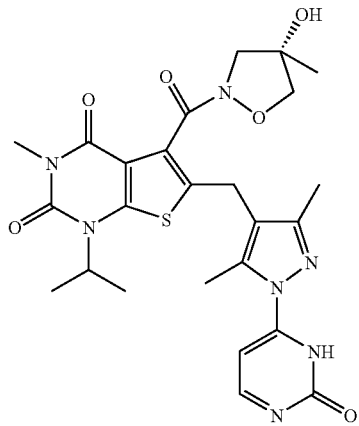

a) 6-[[1-(2,3-Dihydro-2-oxo-4-pyrimidinyl)-3,5-dimethyl-1H-pyrazol-4-yl]methyl]-1,2,3,4-tetrahydro-3-methyl-1-(1-methylethyl)-2,4-dioxo-thieno[2,3-d]pyrimidine-5-carboxylic acid A mixture of the product of example 2 part b) (400 mg), 2,4-dichloropyrimidine (160 mg) and triethylamine (310 µl) in acetonitrile (50 ml) was heated at reflux for 2 hours. The mixture was washed with water and the organics concentrated to dryness to give the sub-title compound as a brown oil (150 mg).

$\delta^1H_{DMSO}$, 1.45 (6H, d), 2.18 (3H, s), 2.57 (3H, s), 3.22 (3H, s), 4.12 (2H, s), 4.35 (s, 1H), 5.44 (1H, d), 7.34-7.41 (1H, m)

b) (4s)-2-[[6-[[1-(2,3-Dihydro-2-oxo-4-pyrimidinyl)-3,5-dimethyl-1h-pyrazol-4-yl]methyl]-1,2,3,4-tetrahydro-3-methyl-1-(1-methylethyl)-2,4-dioxothieno[2,3-d]pyrimidin-5-yl]carbonyl]-4-methyl-4-isoxazolidinol The title compound was prepared from the product of part a) using the method of example 15 part d).

MS (APCI+ve) 556 [M+H]+ $\delta^1H_{DMSO}$, 120° C. 1.40 (3H, s), 1.47 (6H, d), 2.17 (3H, s), 2.54 (3H, s), 3.20 (3H, s), 3.66-3.80 (4H, m), 3.88 (2H, s), 4.46 (sep, 1H), 6.13 (1H, d), 7.87 (2H, d)

EXAMPLE 29

5-[[(4R)-4-Hydroxy-4-methyl-2-isoxazolidinyl]carbonyl]-3-methyl-1-(1-methylethyl)-6-[[5-methyl-3-(trifluoromethyl)-1H-pyrazol-4-yl]methyl]-thieno[2,3-d]pyrimidine-2,4(1H,3H)-dione

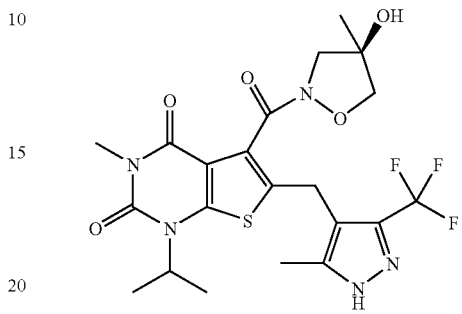

5-[[(4R)-4-Hydroxy-4-methyl-2-isoxazolidinyl]carbonyl]-3-methyl-1-(1-methylethyl)-6-[[5-methyl-3-(trifluoromethyl)-1H-pyrazol-4-yl]methyl]-thieno[2,3-d]pyrimidine-2,4(1H,3H)-dione To a suspension of the product of example 10 part a) (0.130 mg) and (4R)-4-methyl-4-isoxazolidinol hydrochloride (42 mg, prepared by the method of example 1 steps a) to d) using [(2R)-2-methyloxiran-2-yl]methyl 3-nitrobenzenesulfonate) in anhydrous THF (6 ml), was added triethylamine (120 mg) and the mixture was cooled in an icebath. O-(7-azabenzotriazol-1-yl)-N,N,N',N'-tetamethyluronium hexafluorophosphate (120 mg) was added and the mixture was allowed to warm to, whereupon it was stirred for 3 hr. All volatiles were removed in vacuo and the residue was chromatographed (SiO₂/1:1 CH₂Cl₂-EtOAc) to effect primary purification. Further purification by RPHPLC afforded the title compound as a solid (35 mg).

MS (ESI) 516 [M+H]+ $^1H_{DMSO}$ (120° C.) 1.40 (3H, s), 1.46 (6H, d), 2.18 (3H, s), 3.20 (3H, s), 3.6-3.75 (3H, br s+d), 3.81 (1H, d), 3.94 (2H, s), 4.5 (1H, m), 4.95-5.05 (1H, br s) CHN Found C 47.98%, H 4.69%, N 13.48%, S 5.98% C₂₁H₂₄F₃N₅O₅.0.5H₂O requires C 48.09%, H4.8%, N 13.35%, S 6.11%

Pharmacological Data

Inhibition of PMA/Ionomycin-stimulated Peripheral Blood Mononuclear Cell Proliferation The assay for PMA/ionomycin-stimulated PBMC proliferation was performed in 96-well flat-bottomed microtitre plates. Compounds were prepared as 10 mM stock solutions in dimethyl sulfoxide. A 50-fold dilution of this was prepared in RPMI and serial dilutions were prepared from this solution. 10 µl of the 50-fold diluted stock, or dilutions of it, were added to the well to give concentrations in the assay starting at 9.5 µM and going down. Into each well was placed 1×10⁵ PBMC, prepared from human peripheral blood from a single donor, in RPMI1640 medium supplemented with 10% human serum, 2 mM glutamine and penicillin/streptomycin. Phorbol myristate acetate (PMA) (0.5 ng/ml final concentration) and ionomycin (500 ng/ml final concentration) were added to these cells in supplemented RPMI1640 medium (as above) so that the final volume of the assay was 0.2 ml. The cells were incubated at 37° C. in a humidified atmosphere at 5% carbon dioxide for 72 hours. $^3$H-Thymidine (0.5 μCi) was added for the final 6 hours of the incubation. The level of radioactivity incorporated by the cells was then determined and this is a measure of proliferation.

The compounds of the Examples were found to exhibit an $IA_{50}$ value of less than $1\times10^{-6}$ M in the above test. In the following specific examples, Examples 5, 7 and 8 had a $PIA_{50}$ of 7.4, 8.6 and 9.0 respectively in the above test.

The invention claimed is:

1. A compound of formula (1):

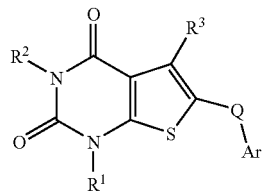

(1)

wherein:

$R^1$ and $R^2$ each independently represent a $C_{1-6}$alkyl, $C_{3-6}$alkenyl, $C_{3-5}$cycloalkyl$C_{1-3}$alkyl or $C_{3-6}$cycloalkyl; each of which may be optionally substituted by 1 to 3 halogen atoms;

$R^3$ is a group CO-G or $SO_2$-G where G is a 5- or 6-membered ring containing a nitrogen atom and a second heteroatom selected from oxygen and sulphur adjacent to the nitrogen; the ring being substituted by at least one group selected from halogen or $C_{1-4}$ alkyl, (which may be optionally substituted by up to five halogen atoms), and optionally substituted by up to a further 4 groups independently selected from halogen, hydroxyl and $C_{1-4}$ alkyl, (which may be optionally substituted by up to five halogen atoms);

Q is $CR^4R^5$ where $R^4$ is hydrogen, fluorine or $C_{1-6}$ alkyl and $R^5$ is hydrogen, fluorine or hydroxy;

Ar is a 5- to 10-membered aromatic ring system wherein up to 4 ring atoms are optionally heteroatoms independently selected from nitrogen, oxygen and sulphur, the ring system being optionally substituted by one or more substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, nitro, cyano, —N($R^6$)$R^7$ and —(CH$_2$)pN($R^8$)$R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy, and $SO_2N(R^6)R^7$, or Ar is optionally substituted by a 5 or 6 membered aromatic ring containing up to 4 heteroatoms independently selected from nitrogen, oxygen and sulphur, and which is optionally substituted by one or more substituents independently selected from $C_{1-4}$alkyl (optionally substituted by 1,2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, nitro, cyano, —N($R^6$)$R^7$ and —(CH$_2$)pN($R^8$)$R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy, and $SO_2 N(R^6)R^7$, p is 1, 2, 3 or 4;

$R^6$ and $R^7$ each independently represent a hydrogen atom, $C_{1-4}$alkanoyl or $C_{1-4}$alkyl, or together with the nitrogen atom to which they are attached form a 5- to 7-membered saturated heterocyclic ring; and $R^8$ and $R^9$ each independently represent a hydrogen atom, $C_{1-4}$alkanoyl or $C_{1-4}$alkyl, or together with the nitrogen atom to which they are attached form a 5- to 7-membered saturated heterocyclic ring;

and pharmaceutically acceptable salts thereof.

2. A compound according to claim 1 in which $R^1$ is ethyl, propyl, butyl or cyclopropyl.

3. A compound according to claim 1 in which $R^2$ is methyl.

4. A compound according to claim 1 in which $R^3$ a group CO-G.

5. A compound according to claim 1 in which Q is $CH_2$.

6. A compound according to claim 1 in which Ar is a 5-membered aromatic ring containing two heteroatoms optionally substituted as defined in claim 1 or Ar is a 9- or 10-membered bicyclic ring containing one, two or three heteroatoms and optionally substituted as defined in claim 1, or phenyl, optionally substituted as defined in claim 1.

7. A compound according to claim 1 in which Ar is a thienyl, pyrazole or thiazole ring each substituted by two or three $C_{1-4}$alkyl, halogen, trifluoromethyl substituents and/or also substituted by a 2-pyrimidinyl or 2-pyridyl group.

8. A compound according to claim 6 wherein Ar is a group of sub-formula (i)

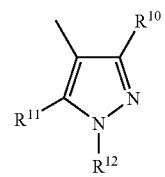

(i)

where $R^{10}$ and $R^{11}$ are independently selected from H, $C_{1-4}$alkyl, or halo$C_{1-6}$alkyl and $R^{12}$ is selected from H, $C_{1-6}$alkyl, or halo$C_{1-6}$alkyl or a 5- to 6-membered aromatic ring system wherein up to 3 ring atoms may be heteroatoms independently selected from oxygen, sulphur and nitrogen, which ring may be optionally substituted by one or more substituents independently selected from $C_{1-4}$alkyl (optionally substituted by 1, 2 or 3 hydroxy groups), $C_{1-4}$alkoxy, halogen, haloalkyl, dihaloalkyl, trihaloalkyl, $C_{1-4}$alkoxy$C_{1-4}$alkyl, $C_{1-4}$alkylthio, $C_{1-4}$alkoxycarbonyl, $C_{2-4}$alkanoyl, nitro, cyano, —N($R^6$)$R^7$ and —(CH$_2$)pN($R^8$)$R^9$, hydroxy, $C_{1-4}$alkylsulphonyl, $C_{1-4}$alkylsulphinyl, carbamoyl, $C_{1-4}$alkylcarbamoyl, di-($C_{1-4}$alkyl)carbamoyl, carboxy, or $SO_2 N(R^6)R^7$.

9. A compound according to claim 8 wherein $R^{10}$ and $R^{11}$ are methyl.

10. A compound according to claim 9 wherein $R^{12}$ is is selected from H, $C_{1-3}$alkyl or a 5- to 6-membered aromatic ring system wherein up to 3 ring atoms may be heteroatoms independently selected from oxygen, sulphur and nitrogen, optionally substituted by hydroxyl.

11. A compound selected from the group consisting of:

(S)-2-[[6-[(3,5-Dimethyl-1H-pyrazol-4-yl)methyl]-1,2,3,4-tetrahydro-3-methyl-1-(2-methylpropyl)-2,4-dioxo-thieno[2,3-d]pyrimidin-5-yl]carbonyl]-4-methyl-4-isoxazolidinol, (S)-2-[[6-[(3,5-Dimethyl-1H-pyrazol-4-yl)methyl]-1,2,3,4-tetrahydro-3-methyl-1-(2-methylethyl)-2,4-dioxo-thieno[2,3-d]pyrimidin-5-yl]carbonyl]-4-methyl-4-isoxazolidinol, 1-Cyclopropyl-6-[(3,5-dimethyl-1H-pyrazol-4-yl)methyl]-5-[[(4S)-4-hydroxy-4-methyl-2-isoxazolidinyl]carbonyl]-3-methyl-thieno[2,3-d]pyrimidine-2,4(1H,3H)-dione, (S)-2-[[6-[(1H-1,2,3-Benzotriazol-1-yl)methyl]-1,2,3,4-tetrahydro-3-methyl-1-(1-methylethyl)-2,4-dioxo-thieno[2,3-d]pyrimidin-5-yl]carbonyl]-4-methyl-4-isoxazolidinol, (S)-2-[[6-[(4,5-Dichloro-2-methyl-1H-imidazol-1-yl)methyl]-1,2,3,4-tetrahydro-1-ethyl-3-methyl-2,4-dioxo-thieno[2,3-d]pyrimidin-5-yl]carbonyl]-4-methyl-4-isoxazolidinol, 5-[[(4S)-4-Hydroxy-4-methyl-2-isoxazolidinyl]carbonyl]-3-methyl-1-(2-methylpropyl)-6-(1H-pyrrolo[2,3-b]pyridin-3-ylmethyl)thieno[2,3-d]pyrimidine-2,4-(1H,3H)-dione, (4S)-4-methyl-2-[[1,2,3,4-tetrahydro-3-methyl-2,4-dioxo-1-propyl-6-(4-quinolinylmethyl)thieno[2,3-d]pyrimidin-5-yl]carbonyl]-4-isoxazolidinol, (4S)-2-[[6-[(2,4-Dichloro-5-thiazolyl)methyl]-1,2,3,4-tetrahydro-3-methyl-1-(2-methylpropyl)-2,4-dioxo-thieno[2,3-d]pyrimidin-5-yl]carbonyl]-4-methyl-4-isoxazolidinol, (4S)-2-[[6-[(3-Bromo-2-thienyl)methyl]-1,2,3,4-tetrahydro-3-methyl-1-(2-methylpropyl)-2,4-dioxo-thieno[2,3-d]pyrimidin-5-yl]carbonyl]-4-methyl-4-isoxazolidinol, 5-[[(4S)-4-Hydroxy-4-methyl-2-isoxazolidinyl]carbonyl]-3-methyl-1-(1-methylethyl)-6-[[5-methyl-3-(trifluoromethyl)-1H-pyrazol-4-yl]methyl]-thieno[2,3-d]pyrimidine-2,4(1H,3H)-dione, 6-[[3,5-Dimethyl-1-(2-pyridinyl)-1H-pyrazol-4-yl]methyl]-5-[[(4S)-4-hydroxy-4-methyl-2-isoxazolidinyl]carbonyl]-3-methyl-1-(1-methylethyl)thieno[2,3-d]pyrimidine-2,4-(1H,3H)-dione, 5-[[(4S)-4-Hydroxy-4-methyl-isoxazolidinyl]carbonyl]-3-methyl-1-(1-methylethyl)-6-(1H-pyrrolo[2,3-b]pyridin-3-ylmethyl)-thieno[2,3-d]pyrimidine-2,4(1H,3H)-dione, (4S)-2-[[6-[[3,5-Dimethyl-1-(4-pyridinyl)-1H-pyrazol-4-yl]methyl]-1,2,3,4-tetrahydro-3-methyl-1-(1-methylethyl)-2,4-dioxo-thieno[2,3-d]pyrimidin-5-yl]carbonyl]-4-methyl-4-isoxazolidinol, (4S)-2-[[6-[[3,5-Dimethyl-1-(2-pyrimidinyl)-1H-pyrazol-4-yl]methyl]-1,2,3,4-tetrahydro-3-methyl-1-(1-methylethyl)-2,4-dioxo-thieno[2,3-d]pyrimidin-5-yl]carbonyl]-4-methyl-4-isoxazolidinol, 5-[[(4S)-4-Hydroxy-4-methyl-2-isoxazolidinyl]carbonyl]-3-methyl-1-(1-methylethyl)-6-[(1-phenyl-1H-pyrazol-4-yl)methyl]-thieno[2,3-d]pyrimidine-2,4-(1H,3H)-dione, 6-[(8-Fluoroquinolin-4-yl)methyl]-5-{[(4S)-4-hydroxy-4-methylisoxazolidin-2-yl]carbonyl}-1-isopropyl-3-methylthieno[2,3-d]pyrimidine-2,4(1H,3H)-dione, 5-{[(4S)-4-Hydroxy-4-methylisoxazolidin-2-yl]carbonyl}-1-isopropyl-3-methyl-6-(4-pyrimidin-2-ylbenzyl)thieno[2,3-d]pyrimidine-2,4(1H,3H)-dione, 5-[[(4S)-4-Hydroxy-4-methyl-2-isoxazolidinyl]carbonyl]-3-methyl-1-(1-methylethyl)-6-[(5-(2-pyridinyl)-2-thienyl)methyl]-thieno[2,3-d]pyrimidine-2,4-(1H,3H)-dione, 6-[(1,3-Dimethyl-1H-5-pyrazolyl)methyl]-5-[[(4S)-4-hydroxy-4-methyl-2-isoxazolidinyl]carbonyl]-3-methyl-1-(1-methylethyl)-thieno[2,3-d]pyrimidine-2,4-(1H,3H)-dione, 6-[(3,5-Dimethyl-4-isothiozolyl)methyl]-5-[[(4S)-4-hydroxy-4-methyl-2-isoxazolidinyl]carbonyl]-3-methyl-1-(1-methylethyl)thieno[2,3-d]pyrimidine-2,4-(1H,3H)-dione, 5-[[(4S)-4-Hydroxy-4-methyl-2-isoxazolidinyl]carbonyl]-3-methyl-1-(1-methylethyl)-6-[[1-(2-thiazolyl)-1H-pyrazol-4-yl]methyl]thieno[2,3-d]pyrimidine-2,4-(1H,3H)-dione, 6-[(4-Fluorophenyl)methyl]-5-[[(4S)-4-hydroxy-4-methyl-2-isoxazolidinyl]carbonyl]-3-methyl-1-(1-methylethyl)thieno[2,3-d]pyrimidine-2,4-(1H,3H)-dione, 5-[[(4S)-4-Hydroxy-4-methyl-2-isoxazolidinyl]carbonyl]-3-methyl-1-(1-methylethyl)-6-(1H-1,2,3-triazol-1-ylmethyl)thieno[2,3-d]pyrimidine-2,4-(1H,3H)-dione, 6-[(6-Chloroimidazo[1,2-a]pyridin-3-yl)methyl]-5-[[(4S)-4-hydroxy-4-methyl-2-isoxazolidinyl]carbonyl]-3-methyl-1-(1-methylethyl)thieno[2,3-d]pyrimidine-2,4-(1H,3H)-dione, 5-[[(4S)-4-hydroxy-4-methylisoxazolidin-2-yl]carbonyl]-3-methyl-1-(1-methylethyl)-6-[[4-(2-pyridinyl)phenyl]methyl]-thieno[2,3-d]pyrimidine-2,4(1H,3H)-dione, (4S)-4-Methyl-2-[[1,2,3,4-tetrahydro-3-methyl-1-(1-methylethyl)-6-[[5-methyl-1-(2-pyrimidinyl)-3-(trifluoromethyl)-1H-pyrazol-4-yl]methyl]-2,4-dioxothieno[2,3-d]pyrimidin-5-yl]carbonyl]-4-isoxazolidinol, (4S)-2-[[6-[[3,5-Dimethyl-1-(2-pyrimidinyl)-1H-pyrazol-4-yl]methyl]-1,2,3,4-tetrahydro-3-methyl-1-(1-methylethyl)-2,4-dioxothieno[2,3-d]pyrimidin-5-yl]carbonyl]-4-ethyl-4-isoxazolidinol, (4S)-2-[[6-[[1-(2,3-Dihydro-2-oxo-4-pyrimidinyl)-3,5-dimethyl-1H-pyrazol-4-yl]methyl]-1,2,3,4-tetrahydro-3-methyl-1-(1-methylethyl)-2,4-dioxothieno[2,3-d]pyrimidin-5-yl]carbonyl]-4-methyl-4-isoxazolidinol, 5-[[(4R)-4-Hydroxy-4-methyl-2-isoxazolidinyl]carbonyl]-3-methyl-1-(1-methylethyl)-6-[[5-methyl-3-(trifluoromethyl)-1H-pyrazol-4-yl]methyl]-thieno[2,3-d]pyrimidine-2,4-(1H,3H)-dione, and pharmaceutically acceptable salts thereof.

12. A pharmaceutical composition comprising a compound of formula (1) or a pharmaceutically acceptable salt thereof as defined in claim 1 and a pharmaceutical carrier.

13. A method of treating asthma in a patient suffering from asthma, which comprises administering to the patient a therapeutically effective amount of a compound of formula (1) or a pharmaceutically acceptable salt thereof as defined in claim 1.

14. A process for the preparation of a compound of formula (1) according to claim 1 which comprises one of the following reactions:

a) when $R^3$ is a group COG, reacting a compound of the formula (10):

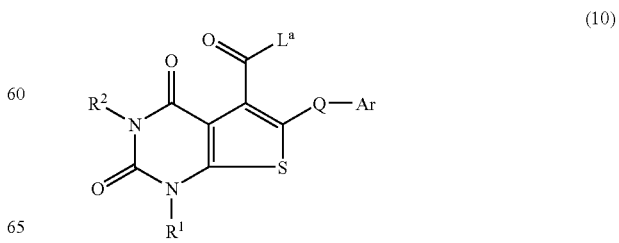

(10)

with G-H;

b) when Q is methylene, reacting a compound of the formula (11):

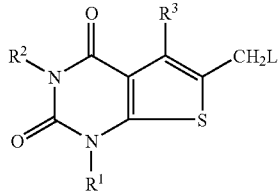
(11)

with a compound of the formula Ar—H;

c) when Q is methylene, reducing a compound of the formula (12):

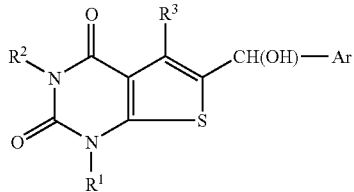
(12)

d) reacting a compound of the formula (11) or (13) to form Ar by primary ring synthesis:

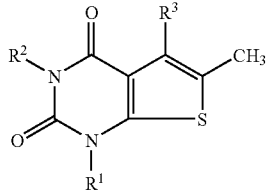
(13)

e) reacting a compound of the formula (14) with $R^1$-$L^2$:

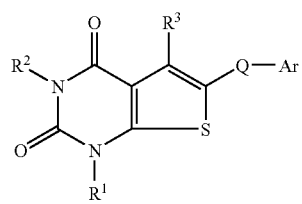
(14)

or f) when $R^3$ is $SO_2G$ reacting a compound of formula (15)

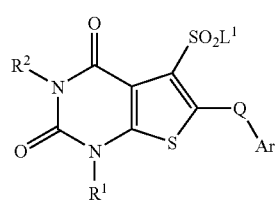
(15)

with a compound G-H, wherein $L^a$, L, $L^1$ and $L^2$ are leaving groups and $R^1$, $R^2$, $R^3$, G, Q and Ar are as defined in claim 1 the process optionally comprises the steps of protecting and deprotecting $R^1$, $R^2$, $R^3$, Q or Ar, and optionally after a), b), c), d), e) or f), the process comprises the step of converting the compound of the formula (1) into a further compound of formula (1) and/or forming a pharmaceutically acceptable salt thereof.

\* \* \* \* \*

UNITED STATES PATENT AND TRADEMARK OFFICE
CERTIFICATE OF CORRECTION

PATENT NO. : 7,384,951 B2
APPLICATION NO. : 10/542197
DATED : June 10, 2008
INVENTOR(S) : Simon David Guile It is certified that error appears in the above-identified patent and that said Letters Patent is hereby corrected as shown below:

Title Page, Column 1, (30)
FOREIGN APPLICATION PRIORITY DATA
Line 1, delete "0300119" insert -- 0300119-5 --

Title Page, Column 2, (56)
OTHER PUBLICATIONS
Line 5, delete "V.[1)]" insert -- V. --

Title Page, Column 2, (57)
ABSTRACT
Line 11, delete "5-10-" insert -- 5- to 10- --
Line 16, delete "pharmaccutically" insert -- pharmaceutically --
Line 19, delete "immunosuppressive" insert -- immunosuppression --

Column 51
Line 57, delete "1,2" insert -- 1, 2 --
Lines 63-64, delete "$SO_2 N(R^6)R^7$," insert -- $SO_2N(R^6)R^7$, --

Column 52
Line 12, after "$R^3$" insert -- is --
Line 51, delete "$SO_2 N(R^6)R^7$." insert -- $SO_2N(R^6)R^7$. --
Line 54, after "$R^{12}$ is" delete -- is --

Column 54
Line 53, delete "COG," insert -- CO-G, --

UNITED STATES PATENT AND TRADEMARK OFFICE
CERTIFICATE OF CORRECTION

PATENT NO. : 7,384,951 B2
APPLICATION NO. : 10/542197
DATED : June 10, 2008
INVENTOR(S) : Simon David Guile It is certified that error appears in the above-identified patent and that said Letters Patent is hereby corrected as shown below:

Column 56
Line 15, delete "$SO_2G$" insert -- $SO_2$-G --
Line 30, after "claim 1" insert -- , --

Signed and Sealed this

Nineteenth Day of August, 2008

JON W. DUDAS
*Director of the United States Patent and Trademark Office*